(12) United States Patent
Yano et al.

(10) Patent No.: US 6,649,623 B1
(45) Date of Patent: Nov. 18, 2003

(54) CYCLIC AMINE DERIVATIVES AND USE THEREOF

(75) Inventors: Toshisada Yano, Osaka (JP); Isako Sakaguchi, Koka-gun (JP); Goro Katsuura, Koka-gun (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 09/889,729

(22) PCT Filed: Jan. 28, 2000

(86) PCT No.: PCT/JP00/00445

§ 371 (c)(1),
(2), (4) Date: Jul. 20, 2001

(87) PCT Pub. No.: WO00/46194

PCT Pub. Date: Aug. 10, 2000

(30) Foreign Application Priority Data

Feb. 8, 1999 (JP) ............................................. 11-029435

(51) Int. Cl.$^7$ ............................. A61K 31/44; A61P 3/04
(52) U.S. Cl. ........................ 514/277; 546/339; 546/340; 546/342; 546/344
(58) Field of Search ................................. 546/339, 340, 546/342, 344; 514/277

(56) References Cited

U.S. PATENT DOCUMENTS

| | | |
|---|---|---|
| 4,267,183 A | 5/1981 | Johnson et al. |
| 4,645,771 A | 2/1987 | Mills |

FOREIGN PATENT DOCUMENTS

| | | | |
|---|---|---|---|
| EP | 269363 | * | 11/1987 |
| EP | 0 978 512 | | 2/2000 |
| GB | 2 045 750 | | 11/1980 |
| WO | 99/48888 | | 9/1999 |

OTHER PUBLICATIONS

Petrow et al, "Some N–substituted derivatives, etc" CA 57: 62636 (1962).*
DeSantis, Jr., et al., Journal of Pharmaceutical Sciences, 65(10), pp. 1479–1484 (1976).
Möhrle et al., Arch. Pharm. (Weinheim), 323(2), pp. 109–115 (1990).
Flann et al., J. Am. Chem. Soc., 109(20), pp. 6097–6107 (1987).
Takemura et al., Chem. Pharm. Bull., 29(10), pp. 3026–3032 (1981).
Ding et al., Synthetic Communications, 20(2), pp. 227–230 (1990).
Chapman et al., J. Chem. Soc. (C), (16), pp. 2269–2272 (1970).

* cited by examiner

*Primary Examiner*—Patricia L. Morris
(74) *Attorney, Agent, or Firm*—Wenderoth, Lind & Ponack, L.L.P.

(57) ABSTRACT

A composition for use as an antiobestic agent and preventive or therapeutic agent for diabetes, containing a compound of the formula (I):

$$A{-}(CH_2)_m{-}X{-}(CH_2)_n{-}N{<}(CH_2)_p \quad (I)$$

wherein, A is optionally substituted aryl or optionally substituted heteroaryl;
X is O, S, NR wherein R is hydrogen or lower alkyl, or single bond;
m is an integer of 0 to 4;
n is an integer of 1 to 5;
p is an integer of 1 to 3, pharmaceutically acceptable salt, prodrug or hydrate thereof.

13 Claims, No Drawings

CYCLIC AMINE DERIVATIVES AND USE THEREOF

TECHNICAL FIELD

The present invention relates to cyclic amine derivatives and use thereof. These derivatives are useful for pharmaceutical compositions such as an antiobestic agent and a preventive or therapeutic agent for diabetes.

BACKGROUND ART

Nowadays, while dietary life is rich and living environment becomes convenient, the patients of obesity keep on increasing. Along with the increase thereof, other various circulatory system diseases such as diabetes, hypertension and hyperlipemia are also spreading as life habit diseases. As the basic therapy for obesity, the diet therapy and the functional therapy have been adopted. When their therapy are not so effective or the patients are of excessive obesity type, the medical therapy, administering a feeding deterrent agent such as 5-HT antagonist, has been conducted. However, the feeding deterrent agent can not essentially improve the obese physical constitution because it does not decompose lipid in obese cells. Moreover, when the feeding deterrent agent is administered to patients so as to excessively repress the appetite of patients, the amount of nutrition-intake in the daily life decreases to less than the minimum level to lead the health control problem. Further, since the feeding deterrent agent acts on the central nervous system, side effects to brain are concerned. Therefore, the feeding deterrent agent is usually used as a supplement in the basic therapy. On the other hand, the pharmacological effect of leptin, a protein produced by an obese gene, had been considered as feeding deterrent effect in the beginning of the research. However, the recent study has revealed that the main effect is the acceleration of lipid decomposition by fever production in fat cells. Namely, it is expected that the stimulation of leptin-release leads to the essential treatment of obesity. (Halaas, J. L., et al. (1995) Weight-reducing effects of the blood protein encoded by the obese gene. Science, 269: 543–546).

Further, diabetes mellitus is usually classified into two types: insulin-dependence (type I, IDDM) accompanied with the decrease of insulin-producing cells and non insulin-dependence (type II, NIDDM) which is considered to be generated by the decrease of insulin sensibility. As the clinical situation, 90% or more of the diabetes mellitus patients are involved in the latter. In the non insulin-dependence diabetes mellitus (type II diabetes mellitus), while the concentration of insulin in blood is high, the sensibility of somatic cells to insulin is decreased due to insulin-resistance. Thus, the intake of glucose existing in blood into somatic cells is inhibited. As the therapeutic agent for type II diabetes mellitus which can improve the insulin resistance, thiazolidine derivatives and the like are under development.

In J. Pharm. Pharmacol. 1962, 14, 16, some tetrahydropyridine derivatives are described as possessing an antihypertensive effect without any other use disclosed.

Therefore, it has been desired to develop a novel antiobestic agent, preferably, which can be safely used without the excessive feeding deterrent. Further needed is a novel preventive or therapeutic agent for diabetes mellitus, especially type II diabetes mellitus, which is one of the diseases associated with obesity.

DISCLOSURE OF INVENTION

The present inventors have intensively studied to find out that cyclic amine derivatives have various pharmacological effects such as reducing body weight, lowering the concentration of insulin and glucose in blood and/or increasing the concentration of leptin in blood and so they are for use as a preventive or therapeutic agent for obesity and/or diabetes and the like, whereby accomplishing the present invention shown below.

(1) A composition for use as an antiobestic agent, containing a compound of the formula (I):

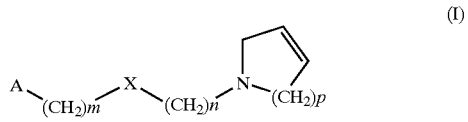

wherein A is optionally substituted aryl or optionally substituted heteroaryl; X is O, S, N R wherein R is hydrogen or lower alkyl, or a single bond;

m is an integer of 0 to 4;

n is an integer of 1 to 5;

p is an integer of 1 to 3, pharmaceutically acceptable salt, prodrug or hydrate thereof.

(2) The composition for use as an antiobestic agent described in above (1) containing a compound wherein A is optionally substituted phenyl, optionally substituted pyridyl, optionally substituted isoquinolyl, optionally substituted quinolyl, optionally substituted thienyl, optionally substituted furyl, optionally substituted benzothienyl, or optionally substituted benzofuryl.

(3) The composition for use as an antiobestic agent described in above (1) containing a compound wherein A is optionally substituted phenyl or optionally substituted benzothienyl.

(4) The composition for use as an antiobestic agent described in above (1) containing a compound wherein A is phenyl substituted with same or different, one to three group(s) selected from the group consisting of halogen, hydroxy, lower alkyl, halogenated lower alkyl, piperidyl (lower) alkyl, lower alkoxy, halogenated lower alkoxy, carboxy lower alkoxy, optionally substituted aryl, optionally substituted aryloxy and optionally substituted aryl (lower) alkoxy.

(5) The composition for use as an antiobestic agent described in above (1) containing a compound wherein X is O or NR wherein R is methyl or ethyl.

(6) The composition for use as an antiobestic agent described in above (1) containing a compound wherein X is O.

(7) The composition for use as an antiobestic agent described in above (1) containing a compound wherein m is 0.

(8) The composition for use as an antiobestic agent described in above (1) containing a compound wherein n is 2 or 3.

(9) The composition for use as an antiobestic agent described in above (1) containing a compound wherein p is 2.

(10) The composition for use as an antiobestic agent described in above (1) containing a compound wherein A is optionally substituted phenyl or optionally substituted benzothienyl; X is O or NR wherein R is methyl or ethyl; m is 0; n is 2 or 3; and p is 2.

(11) The composition for use as an antiobestic agent described in above (1) containing a compound wherein A is optionally substituted phenyl; X is O; m is 0; n is 2 or 3; and p is 2.

(12) A composition for use as a preventive or therapeutic agent for diabetes containing a compound described in any one of above (1) to (11).

(13) A composition for use as an agent for increasing concentration of leptin in blood containing a compound described in any one of above (1) to (11).

(14) A compound of the formula (II):

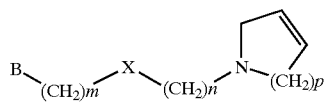

wherein B is

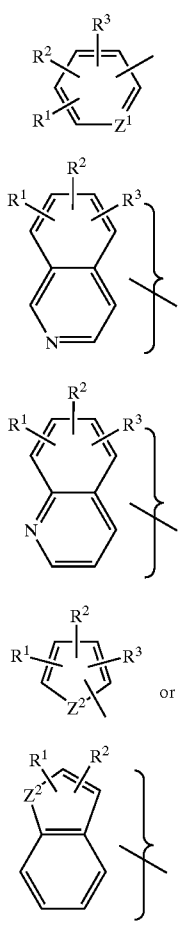

wherein $R^1$, $R^2$ and $R^3$ are each independently hydrogen, halogen, hydroxy, lower alkyl, halogenated lower alkyl, piperidyl (lower) alkyl, lower alkoxy, halogenated lower alkoxy, carboxy lower alkoxy, optionally substituted aryl, optionally substituted aryloxy, or optionally substituted aryl (lower) alkoxy; $Z^1$ is CH or N; $Z^2$ is O or S;

X is O, S, NR wherein R is hydrogen or lower alkyl, or a single bond;

m is an integer of 0 to 4;

n is an integer of 1 to 5;

p is an integer of 1 to 3, provided that when B is (a), X is O, m is 0 and p is 2, the following (1) and (2) are excluded: (1) n is 2 and B is 3,4-dimethylphenyl, 4-t-butylphenyl, 4-(t-butyl-$CH_2C$ $(CH_3)_2$)phenyl, 4-isopentylphenyl, 2-isopropyl-5-methylphenyl, 3-methoxyphenyl or 2-Cl-4-Br-phenyl, (2) n is 3 and B is 2,6-dimethylphenyl, phamaceutically acceptable salt, prodrug, or hydrate thereof.

(15) The compound described in above (14) excluding that X is O; m is 0; n is 2 or 3; p is 2; B is (a); one or two of $R^1$, $R^2$ and $R^3$ is lower alkyl and the other is hydrogen.

(16) The compound described in above (14) excluding a compound wherein X is O; m is 0; n is 2; p is 2; B is (a); $R^1$ is lower alkoxy, $R^2$ and $R^3$ are hydrogens.

(17) The compound described in any one of above (14) to (16) wherein B is (a) or (e).

(18) The compound described in any one of above (14) to (16) wherein $R^1$ is halogen; $R^2$ and $R^3$ are each independently hydrogen, halogen or lower alkyl.

(19) The compound described in above (18) wherein $R^1$ is halogen; $R^2$ and $R^3$ are each independently hydrogen or halogen.

(20) The compound described in any one of above (14) to (16) wherein $R^1$ is halogenated lower alkyl, $R^2$ is hydrogen or halogenated lower alkyl, $R^3$ is hydrogen.

(21) The compound described in any one of above (14) to (16) wherein X is O or NR wherein R is methyl or ethyl.

(22) The compound described in above (21) wherein X is O.

(23) The compound described in any one of above (14) to (16) wherein m is 0.

(24) The compound described in any one of above (14) to (16) wherein n is 2 or 3.

(25) The compound described in above (24) wherein p is 2.

(26) The compound described in above (14) wherein B is (a) and $R^1$ is halogen, $R^2$ and $R^3$ are each independently hydrogen, halogen or lower alkyl; X is O; m is 0; n is 3; p is 2.

(27) The compound described in above (26) wherein B is (a) and $R^1$ is halogen; $R^2$ and $R^3$ are each independently hydrogen or halogen; X is O; m is 0; n is 3; p is 2.

(28) The compound described in above (14) wherein B is (a) and $R^1$ is halogenated lower alkyl, $R^2$ is hydrogen or halogenated lower alkyl, $R^3$ is hydrogen, X is O; m is 0; n is 3; p is 2.

(29) A pharmaceutical composition containing a compound described in any one of above (14) to (28).

(30) A composition for use as an antiobestic agent containing a compound described in any one of above (14) to (28).

(31) A composition for use as a preventive or therapeutic agent for diabetes containing a compound described in any one of above (14) to (28).

(32) A composition for use as an agent for increasing concentration of leptin in blood, containing a compound described in any one of above (14) to (28).

(33) A method for preventing or treating obese, which comprises administering a compound described in any one of above (1) to (11) or (14) to (28).

(34) A method for preventing or treating diabetes, which comprises administering a compound described in any one of above (1) to (11) or (14) to (28).

(35) A method for increasing concentration of leptin in blood, which comprises administering a compound described in any one of above (1) to (11) or (14) to (28).

(36) Use of a compound described in any one of above (1) to (11) or (14) to (28) for production of an antiobestic agent.

(37) Use of a compound described in any one of above (1) to (11) or (14) to (28) for production of a preventive or therapeutic agent for diabetes mellitus.

(38) Use of a compound described in any one of above (1) to (11) or (14) to (28) for production of an agent for increasing concentration of leptin in blood.

BEST MODE FOR CARRYING OUT THE INVENTION

One of the structural features of compound (I) is to have an unsaturated 5- to 7-membered, preferably 6-membered cyclic amine.

Terms used herein are explained below. Unless otherwise mentioned, each term, by itself or as part of another, has the following meaning.

Examples of lower alkyl include a straight or branched C1 to C6 alkyl such as methyl, ethyl, n-propyl, i-propyl, n-butyl, i-butyl, sec-butyl, t-butyl, n-pentyl, i-pentyl, neo-pentyl, tert-pentyl, n-hexyl, and the like and preferred is C1 to C4 alkyl, more preferred is methyl or ethyl.

Lower alkoxy includes oxy connected with the above lower alkyl, such as methoxy, ethoxy, i-propoxy, tert-butoxy, pentyloxy, hexyloxy and the like.

Halogen means F, Cl, Br and I.

Halogenated lower alkyl is preferably trihalogenated methyl (e.g., —CF$_3$) and the like.

Halogenated lower alkoxy is preferably trihalogenated methoxy (e.g., —OCF$_3$) and the like.

Aryl means a monocyclic or fused aromatic hydrocarbon group such as phenyl, α-naphthyl, β-naphthyl, anthoryl, indenyl, phenantryl and the like and preferred is phenyl.

Heteroaryl means an aromatic monocyclic or polycyclic group containing the same or different hetero atom selected from O, S and N.

The monocyclic group includes a 5- to 6-membered cyclic group containing one to four hetero atom, such as pyridyl, furyl, thienyl, tetrazolyl, pyrolyl, pyrazolyl, imidazolyl, oxazolyl, thiazolyl, thiaziazolyl, oxazinyl, triazinyl and the like and preferably pyridyl (e.g., 2-pyridyl), furyl (e.g., 2-furyl) or thienyl (e.g., 2-thienyl).

The polycyclic group includes a 2- or 3-cyclic hetero cyclic group containing one to five hetero atom and preferred is a 8- to 14-membered cyclic group such as quinolyl, isoquinolyl, indoryl, benzoimidazolyl, indazolyl, indorydinyl, benzofuryl, benzothienyl, acrydinyl, phenanthrydinyl and the like, and preferably quinolyl (e.g., 4-quinolyl), isoquinolyl (e.g., 5-isoquinolyl), benzothienyl (e.g., 5-benzothienyl), benzofuryl (e.g., 5-benzofuryl).

When the above aryl or heteroaryl is substituted, examples of the substituent include a same or different group selected from the group consisting of halogen, lower alkyl, lower alkoxy, lower alkylthio, hydroxy, amino, carboxy, cyano, nitro, lower alkylcarbonyl, lower alkoxycarbonyl, halogenated lower alkyl, halogenated lower alkoxy, pyperidyl (lower) alkyl, carboxy (lower) alkoxy, optionally substituted aryl, optionally substituted aryloxy, optionally substituted aryl (lower) alkoxy and the like. These may be located at any substitutable position in a range of one to five, preferably one to three. Furthermore, as each substituent of the optionally substituted aryl, the optionally substituted aryloxy and the optionally substituted aryl (lower) alkoxy, exemplified are lower alkyl, halogen, halogenated lower alkyl, halogenated lower alkoxy and the like.

A is preferably the group exemplified by (a) to (e) in the above B, e.g., optionally substituted phenyl, optionally substituted pyridyl, optionally substituted isoquinolyl, optionally substituted quinolyl, optionally substituted thienyl, optionally substituted furyl, optionally substituted benzothienyl, or optionally substituted benzofuryl. More preferable group is optionally substituted phenyl (substituent: same or different, one to three group selected from the group consisting of halogen, hydroxy, lower alkyl (e.g., methyl, t-Bu), halogenated lower alkyl (e.g., —CF$_3$), piperidyl (lower) alkyl (e.g., 1-piperidylmethyl), lower alkoxy (e.g., methoxy), halogenated lower alkoxy (e.g., —OCF$_3$), carboxy lower alkoxy (e.g., carboxy methyl), optionally substituted aryl (e.g., optionally substituted phenyl (substituent: p-Br)), optionally substituted aryloxy (e.g., optionally substituted phenyl (substituent: trihalogenated lower alkyl (e.g., —CF$_3$))), and optionally substituted aryl (lower) alkoxy (e.g., optionally substituted benzyl oxy (substituent: halogen (e.g., F), lower alkyl (e.g., methyl), trihalogenated lower alkyl (e.g., —CF$_3$))).

X is preferably O or NR wherein R is methyl or ethyl, more preferably O.

m is preferably 0.

n is preferably 1~4, more preferably 3.

p is preferably 2.

The compound (I) includes a new compound, typically the compound (II).

A preferable bond form of each group (a) to (e), defined as B of compound (II) is shown below.

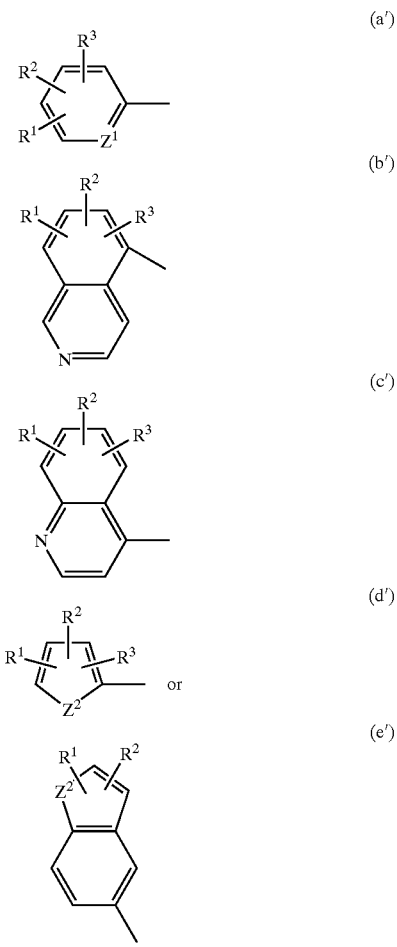

B is preferably a group of (a), more preferably a group of (a'). $Z^1$ is preferably CH and $R^1$ is preferably halogen, $R^2$ and $R^3$ are each preferably independently hydrogen or halogen. More preferably, $R^1$ and $R^2$ are halogen in meta and para positions (esp., Cl), $R^3$ is hydrogen. When $Z^1$ is CH, $Z^1$ may be substituted by each of $R^1$, $R^2$ and $R^3$. As the other preferable embodiment of (a'), exemplified is a compound wherein $Z^1$ is CH, $R^2$ is hydrogen, $R^1$ is a group selected from the group consisting of hydrogen, halogen (e.g., F, Cl, Br), lower alkyl (e.g., methyl, tert-butyl), lower alkoxy (e.g., methoxy) and halogenated lower alkoxy (e.g., $CF_3$), which is substituted at the 2- or 3-position), $R^3$ is optionally substituted phenyloxy wherein the substituent is same or different, one or two groups selected from the group consisting of hydrogen, halogen (e.g., F, Cl, Br), lower alkyl (e.g., methyl, tert-butyl), lower alkoxy (e.g., methoxy), and halogenated lower alkoxy (e.g., $CF_3$), which may be substituted at any of 2- to 6-position.).

One of preferable embodiments of the compound (II) includes that wherein p=2, n=3, X=O, m=0, B=(a'), $R^2$=hydrogen and $R^3$=optionally substituted phenyloxy such as compounds shown by formula (IIa) in Example 52. The compound (II) hereinafter, included in the scope of compound (I), may be referred to as compound (I).

The preparation of the compound (I) is exemplified below and the compound (II) can be prepared likewise.

(Preparation 1)

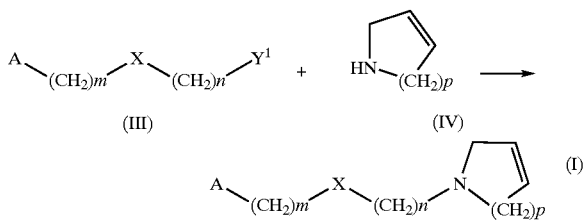

wherein, $Y^1$ is a leaving group such as halogen, the other symbols are the same meaning as described above.

The compound (III) and the compound (IV) are reacted, if necessary in the presence of a base, to give the compound (I). As the base, carbonate ($K_2CO_3$, $Na_2CO_3$ and the like), NaOH, tertiary amine and the like can be used. Furthermore, KI may be used together with them. As a solvent, $CH_3CN$, dimethylformamide (DMF), dimethylsulfoxide (DMSO) and the like can be used. The reaction temperature is usually about 10 to 200° C., preferably room temperature to about 110° C., reaction time is several hours to several ten hours, preferably about one to 20 hours, more preferably about 3 to 15 hours. The compound (III) and the compound (IV) are prepared by known reactions or may be commercially available products.

(Preparation 2)

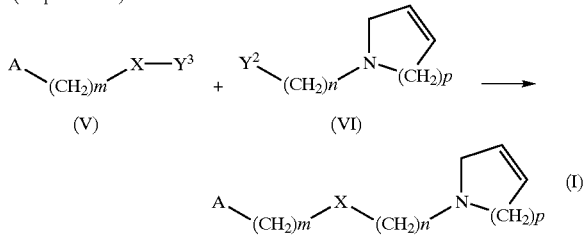

wherein $Y^2$ is halogen or the like, $Y^3$ is hydrogen in the case of X=O, S or a leaving group (e.g., halogen, —$COCF_3$ and the like), in the case of X=NR, the other symbols are the same meaning as described above.

The compound (V) and the compound (VI) are reacted, if necessary in the presence of a base, to give the compound (I). As the base, carbonate ($K_2CO_3$, $Na_2CO_3$ and the like), NaOH, tertiary amine and the like can be used. Moreover, KI may be used together with them. As a solvent, $CH_3CN$, dimethylformamide (DMF), dimethylsulfoxide (DMSO) and the like can be used. The reaction temperature is usually about 10 to 200° C., preferably room temperature to about 110° C. The reaction time is several hours to several ten hours, preferably about 1 to 20 hours, more preferably about 3 to 15 hours. The compound (V) and the compound (VI) are prepared by known reactions or may be commercially available products.

Prior to the above each reaction, a functional group may be protected by a method well known to skilled persons and if necessary deprotected after the reaction.

Examples of the pharmaceutically acceptable salt of compound (I) include salts formed with inorganic bases, ammonia, organic bases, inorganic acids, organic acids, basic amino acids, halogen ions or the like, and inner molecular salts. Examples of the inorganic base include alkaline metal (e.g., Na, K) and alkaline earth metal (e.g., Ca, Mg). Examples of the organic base include trimethylamine, triethylamine, choline, procaine, ethanol amine and the like. Examples of the inorganic acid include hydrochloric acid, hydrobromic acid, sulfuric acid, nitric acid, and phosphoric acid and the like. Examples of the organic acid include p-toluene sulfonic acid, methanesulfonic acid, formic acid, trifluoroacetic acid and maleic acid and the like. Examples of the basic amino acid include lysine, arginine, ornithine, histidine and the like.

Compound (I) May be Hydrate.

Prodrug means a derivative of the present invention compound, which has a chemically or metabolically decomposable group and is converted, by solvolysis or under physiological conditions, to a compound of present invention which is pharmaceutically active in vivo. A preparation of an appropriate prodrug-derivative is described in, e.g., Design of Pro agents Elsevier, Amsterdam 1985. When the compound of present invention has a carboxy group, examples of the prodrug include an ester derivative prepared by reacting a proper alcohol with an original acidic compound or an amide derivative prepared by reacting a proper amine with an original acidic compound. When the compound of present invention has a hydroxyl group, examples of the prodrug include an acyloxy derivative prepared by reacting a proper acylharide or a proper acidic anhydride with a hydroxyl group-containing compound. When the compound of present invention has an amino group, examples of prodrug include an amide derivative prepared by reacting a proper acidic halogenated compound or a proper mixed acidic anhydride with an amino group-containing compound.

The present compound can be administered orally or parenterally to animal including man as a pharmaceutical composition, especially antiobestic agent or preventive or therapeutic agent for diabetes. Examples of the administered form include granules, tablets, capsules, injections and the like. In formulation, various additives can be used such as excipients, disingrators, binders, lubricants, stabilizers, coloring agents, coating agents if necessary. Although the dosage of the compound of the present invention may vary depending on the age, weight, conditions of the patient, and the administration route and the like, the daily dose for adult can generally be about 20 to 1000 mg for oral administration. For parenteral administration, the daily dose can be about 2 to 10 mg.

As the present compound increases remarkably the concentration of leptin in blood, the preventive and therapeutic effect against various diseases associated with leptin is expected. According to recent study, it is known that leptin activates sympathetic nerve to decompose lipid in the obesity cells. Moreover, it is reported that if leptin concentration rises, the resistance of insulin is improved to the lower insulin concentration. From these results, it is suggested that the present compound and the agent for increasing the concentration of leptin containing the present compound is for use as an antiobestic agent and/or a preventive and therapeutic agent for diabetes mellitus. A more preferable compound of present invention shows potent anti-obesitic effect without repressing feeding deterrent excessively.

Examples of present invention are shown below. The scheme of reaction in Examples 1 to 7 is shown below.

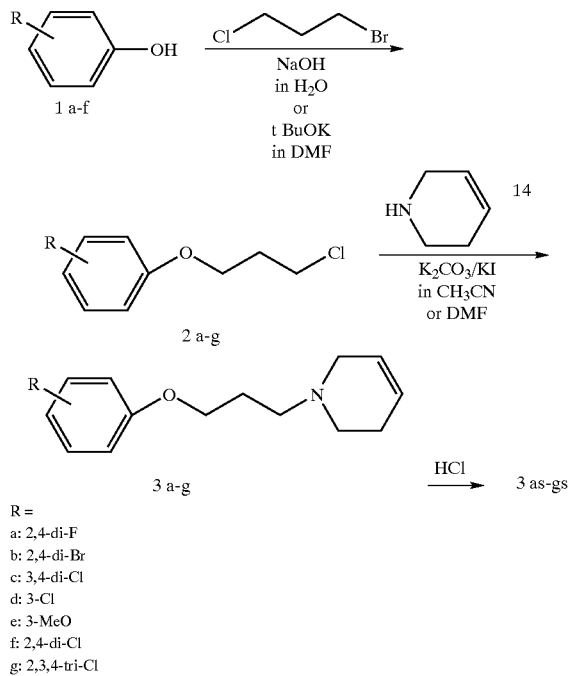

R =
a: 2,4-di-F
b: 2,4-di-Br
c: 3,4-di-Cl
d: 3-Cl
e: 3-MeO
f: 2,4-di-Cl
g: 2,3,4-tri-Cl

EXAMPLE 1

(1) Preparation of 2a; 1-(3-Chloropropoxy)-2,4-difluoro-benzene

To a mixture of (1a) (22.7 g), 1-bromo-3-chrolopropane (74.2 g) and NaOH (11.8 g) was added 250 mL of water, and the mixture was refluxed for 7 hours. The reaction mixture was cooled and extracted with diethyl ether. The organic layer was washed with water and saturated saline, dried over $MgSO_4$ and the solvent was evaporated under reduced pressure. The resultant oily product was distilled under reduced pressure to give 27.6 g (77%) of the compound (2a), boiling point 58~61° C./1 mmHg.

IR ($CHCl_3$). 3085, 3022, 2967, 2883, 1604, 1514, 1470, 1437, 1422, 1389, 1300, 1284, 1259, 1230; NMR ($CDCl_3$) δ (200 $MH_z$); 2.247 (t, J=6 Hz, 2H); 3.770 (t, J=6 Hz, 2H); 4.153 (t, J=6 Hz, 2H); 6.70~7.00 (m, 3H).

(2) Preparation of 3a; 1-[3-(2,4-Difluoro-phenoxy)-propyl]-1,2,3,6-tetrahydro-pyridine To 20 ml of $CH_3CN$ were added (2a) (1.0 g), 1,2,3,6-tetrahydro-pyridine (0.41 g), $K_2CO_3$ (1.34 g) and KI (0.40 g), and the mixture was refluxed for 13 hours. After cooling, the reaction solution was poured to water and the mixture was extracted with ethyl acetate. The organic layer was washed with water and saturated saline, dried over $MgSO_4$ and the solvent was evaporated under reduced pressure. The resultant oily product was purified by silica gel chromatography (toluene/ethyl acetate=1/1~ethyl acetate) to give 0.9 g (73%) of the compound (3a). The product was recrystallized with isopropanol-diethyl ether to give the corresponding hydrochloride (3as) as white crystal. (melting point; 105.5~107.0° C.).

IR ($CHCl_3$); Elementary analysis (%): $C_{14}H_{17}F_2NO.HCl$; Calcd.: C=58.03, H=6.26, N=4.83, Cl=12.24, F=13.11; Found: C=57.85, H=6.23, N=4.89, Cl=12.09, F=13.07; IR (Nujol) (HCl salt); 3415, 2685, 2590, 2561, 2425, 1789, 1661, 1605, 1503, 1469, 1430, 1409, 1384, 1295; NMR ($CDCl_3$) δ (300 $MH_z$) (Free); 2.024 (quint., J=7 Hz, 2H); 2.15~2.25 (m, 2H); 2.55~2.63 (m, 4H); 2.95~3.02 (m, 2H); 4.072 (t, J=6 Hz, 2H); 5.66~5.80 (m, 2H); 6.72~7.00 (m, 3H).

EXAMPLE 2

(1) Preparation of 2b; 2,4-Dibromo-1-(3-chloropropoxy)-benzene

DMF (45 ml) solution containing (1 b) (5.5 g) and tBuOK (2.45 g) was stirred at room temperature for an hour. To the solution was added 1-bromo-3-chrolopropane (6.86 g) and mixed at room temperature for 10 hours. The resultant reaction solution was poured into water and extracted with ethyl acetate. The organic layer was washed with water and saturated saline, dried over $MgSO_4$ and the solvent was evaporated under reduced pressure. The resultant oily product was purified by silica gel chromatography (hexane/toluene=3/1) to give 6.1 g of the compound (2b) (85%).

IR ($CHCl_3$); 3020, 3015, 2968, 2941, 2885, 1579, 1481, 1465, 1444, 1383, 1286, 1263, 1247, 1227; NMR ($CDCl_3$) δ (200 $MH_z$); 2.278 (quint., J=6 Hz, 2H); 3.806 (t, J=6 Hz, 2H); 4.149 (t, J=6 Hz, 2H); 6.787 (d, J=9 Hz, 1H); 7.367 (d-d, J1=9 Hz, J2=3 Hz, 1H); 7.665 (d, J=3 Hz, 1H).

(2) Preparation of 3b; 1-[3-(2,4-Dibromo-phenoxy)-propyl]-1,2,3,6-tetrahydro-pyridine (2b) (1.5 g), 1,2,3,6-tetrahydro-pyridine (0.46 g), $K_2CO_3$ (1.26 g) and KI (0.38 g) were added to 25 ml of $CH_3CN$, and the mixture was refluxed for 13 hours. After cooling, the reaction solution was poured to water and extracted with ethyl acetate. The organic layer was washed with water and saturated saline, dried over $MgSO_4$ and the solvent was evaporated under reduced pressure. The resultant oily product was purified by silica gel chromatography (toluene/ethyl acetate=1/1~ethyl acetate) to give (3b). The product was recrystallized with isopropanol-diethyl ether to give the corresponding hydrochloride (3bs) as white crystals (melting point; 147.5~148.5° C.).

Elementary analysis (%): $C_{14}H_{17}Br_2NO.HCl$; Calcd.: C=40.80, H=4.41, N=3.40, Br=38.83, Cl=8.61, Found: C=40.74, H=4.42, N=3.47, Br=38.77, Cl=8.55, IR (Nujol) (HCl salt); 2678, 2534, 2469, 2415, 1577, 1565, 1480, 1463, 1429, 1409, 1383, 1291, 1267, 1246; NMR ($CDCl_3$) δ (300 $MH_z$) (Free); 2.049 (quint., J=7 Hz, 2H); 2.15~2.23 (m, 2H); 2.584 (t, J=6 Hz, 2H); 2.628 (t, J=7 Hz, 2H); 2.95~3.02 (m, 2H); 4.070 (t, J=6 Hz, 2H); 5.65~5.80 (m, 2H); 6.779 (d, J=9 Hz, 1H); 7.338 (d-d, J1=9 Hz, J2=2 Hz, 1H); 7.649 (d, J=2 Hz, 1H).

EXAMPLE 3

(1) Preparation of 2c; 1,2-Dichloro-4-(3-chloropropoxy)-benzene

Two hundred ml of DMF solution containing (1c) (30 g) and tBuOK (21.1 g) was stirred at room temperature for 2.5 hours. To the solution was added 50 ml of DMF solution containing 1-bromo-3-chloropropane (43.5 g) and mixed at 50° C. for 7 hours. The resultant reaction solution was poured to water and extracted with ethyl acetate. The organic layer was washed with water and saturated saline, dried over $MgSO_4$ and the solvent was evaporated under reduced pressure. The resultant oily product was refluxed under reduced pressure to give 40.6 g of the compound (2c) (92%).

IR ($CHCl_3$); 3079, 2925, 2968, 2936, 2885, 1594, 1578, 1524, 1467, 1445, 1432, 1389, 1295, 1284, 1261, 1229; NMR ($CDCl_3$) δ (200 $MH_z$); 2.231 (quint., J=6 Hz, 2H); 3.731 (t, J=6 Hz, 2H); 4.091 (t, J=6 Hz, 2H); 6.765 (d-d, J1=9 Hz, J2=3 Hz, 1H); 7.009 (d, J=3 Hz, 1H); 7.327 (d, J=9 Hz, 1H).

(2) Preparation of 3c; 1-[3-(3,4-Dichloro-phenoxy)-propyl]-1,2,3,6-tetrahydro-pyridine (2c) (15 g), 1,2,3,6-tetrahydro-pyridine (6.24 g), $K_2CO_3$ (17.3 g) and KI (5.2 g) were added to 100 ml of DMF, and the mixture was stirred at 90° C. for 5 hours and after cooling the reaction solution was poured to water and extracted with ethyl acetate. The organic layer was washed with water and saturated saline, dried over $MgSO_4$ and the solvent was evaporated under reduced pressure. The resultant oily product was purified by silica gel chromatography (ethyl acetate/toluene=1/1~ethyl acetate) to give 14.95 g of (3c) (83%). The product was recrystallized with isopropanol-methanol to give the corresponding hydrochloride (3cs) as white crystals (melting point; 184.5~185.0° C.).

Elementary analysis (%): $C_{14}H_{17}Cl_2NO.HCl$; Calcd.: C=52.11, H=5.62, N=4.34, Cl=32.96, Found: C=51.86, H=5.60, N=4.40, Cl=32.87, IR (Nujol) (HCl salt); 3050, 3035, 2679, 2544, 1717, 1596, 1564, 1462, 1426, 1399, 1380, 1286; NMR ($CDCl_3$) δ (200 $MH_z$) (Free); 2.032 (quint., J=7 Hz, 2H); 2.10~2.25 (m, 2H); 2.50~2.65 (m, 4H); 2.90~3.05 (m, 2H); 3.999 (t, J=6 Hz, 2H); 5.60~5.82 (m, 2H); 6.753 (d-d, J1=9 Hz, J2=3 Hz, 1H); 7.001 (d, J=3 Hz, 1H); 7.300 (d, J=9 Hz, 1H).

EXAMPLE 4

(1) Preparation of 2d; 1-(3-Chloropropoxy)-3-chloro-benzene

To a mixture of (1d) (25 g), 1-bromo-3-chloropropane (82.66 g) and NaOH (13.2 g) was added 250 ml of water and refluxed for 8 hours. After the reaction solution was cooled, the solution was extracted with diethyl ether. The organic layer was washed with water and saturated saline, dried over $MgSO_4$ and the solvent was evaporated under reduced pressure. The resultant oily product was distilled under reduced pressure to give 30.7 g of the compound(2d) (77%), boiling point 78~85° C./1 mmHg.

IR ($CHCl_3$); 3023, 2967, 2936, 1596, 1580, 1482, 1469, 1428, 1389, 1306, 1283, 1247, 1229, 1225, NMR ($CDCl_3$) δ (200 $MH_z$); 2.231 (quint., J=6 Hz, 2H); 3.737 (t, J=6 Hz, 2H); 4.103 (t, J=6 Hz, 2H); 6.75~7.00 (m, 3H); 7.199 (t, J=8 Hz, 1H).

(2) Preparation of 3d; 1-[3-(3-Chlorophenoxy)-propyl]-1,2,3,6-tetrahydro-pyridine (2d) (0.99 g), 1,2,3,6-tetrahydro-pyridine (0.41 g), $K_2CO_3$ (1.34 g) and KI (0.40 g) were added to 20 ml of $CH_3CN$, and the mixture was refluxed for 13 hours. After cooling, the reaction solution was poured to water, extracted with ethyl acetate. The organic layer was washed with water and saturated saline, dried over $MgSO_4$ and the solvent was evaporated under reduced pressure. The resultant oily product was purified by silica gel chromatography (toluene/ethyl acetate=3/1~ethyl acetate) to give 0:95 g of (3d) (78%). The product was recrystallized with isopropanol-diethyl ether to give the corresponding hydrochloride (3ds) as white crystals (melting point; 141.5~142.5° C.).

Elementary analysis (%): $C_{14}H_{18}ClNO.HCl$; Calcd.: C=58.34, H=6.64, N=4.86, Cl=24.60, Found: C=58.05, H=6.60, N=4.90, Cl=24.27, IR (Nujol) (HCl salt); 3087, 2677, 2657, 2591, 2522, 2496, 2437, 1593, 1480, 1461, 1382, 1289; NMR ($CDCl_3$) δ (300 $MH_z$) (Free); 2.006 (quint., J=7 Hz, 2H); 2.15~2.25 (m, 2H); 2.55~2.62 (m, 4H); 2.97~3.05 (m, 2H); 5.62~5.80 (m, 2H); 6.75~7.20 (m, 4H).

EXAMPLE 5

(1) Preparation of 2e; 1-(3-Chloropropoxy)-3-methoxy-benzene

To a mixture of (1e) (10 g), 1-bromo-3-chloropropane (34.2 g) and NaOH (15.48 g) was added 100 ml of water and refluxed for 4 hours. After the reaction solution was cooled, the solution was extracted with diethyl ether. The organic layer was washed with water and saturated saline, dried over $MgSO_4$ and the solvent was evaporated under reduced pressure. The resultant oily product was distilled under reduced pressure to give 13.1 g of the compound (2e) (81%), boiling point 90~93° C./1 mmHg.

IR($CHCl_3$); 3022, 2962, 2940, 2884, 2837, 1601, 1492, 1469, 1454, 1438, 1388, 1287, 1266, 1225, 1214; NMR ($CDCl_3$) δ (300 $MH_z$); 2.229 (quint., J=6 Hz, 2H); 3.743 (t, J=6 Hz, 2H); 3.792 (s, 3H); 4.101 (t, J=6 Hz, 2H); 6.40~6.56 (m, 3H); 7.182 (t, J=8 Hz, 1H).

(2) Preparation of 3e; 1-[3-(3-Methoxy-phenoxy)-propyl]-1,2,3,6-tetrahydro-pyridine (2e) (1.0 g), 1,2,3,6-tetrahydro-pyridine (0.46 g), $K_2CO_3$ (1.38 g) and KI (0.42 g) were added to 25ml of $CH_3CN$ and the mixture was refluxed for 15 hours. After cooling, the reaction solution was poured to water and extracted with ethyl acetate. The organic layer was washed with water and saturated saline, dried over $MgSO_4$ and the solvent was evaporated under reduced pressure. The resultant oily product was purified by silica gel chromatography (toluene/ethyl acetate=3/1~ethyl acetate) to give 0.82 g of (3e) (66%). The product was recrystallized with isopropanol-diethyl ether to give the corresponding hydrochloride (3es) as white crystals (melting point; 142.0~144.0° C.).

Elementary analysis (%): $C_{15}H_{21}NO_2.HCl$; Calcd.: C=63.48, H=7.81, N=4.94, Cl=12.49, Found: C=63.37, H=7.79, N=4.91, Cl=12.24, IR (Nujol) (HCl salt); 3417, 2681, 2594, 2523, 2489, 2424, 1601, 1590, 1495, 1487, 1452, 1389, 1292, 1267; NMR ($CDCl_3$) δ (300 $MH_z$) (Free); 2.012 (quint., J=7 Hz, 2H); 2.15~2.25 (m, 2H); 2.55~2.65 (m, 4H); 2.95~3.05 (m, 2H); 3.785 (s, 3H); 4.017 (t, J=7 Hz, 2H); 5.63~5.80 (m, 2H); 6.45~6.55 (m, 3H); 7.14~7.20 (m, 1H).

EXAMPLE 6

(1) Preparation of 2f; 1,3-Dichloro-4-(3-chloropropoxy)-benzene

Fifty ml of DMF solution containing (1f) (5.6 g) and tBuOK (3.86 g) was stirred at room temperature for 1.5 hours. To the solution, 1-bromo-3-chloropropane (10.83 g) was added and the mixture was stirred at room temperature for 14 hours. The resultant reaction solution was poured to water and extracted with ethyl acetate. The organic layer was washed with water and saturated saline, dried over $MgSO_4$ and the solvent was evaporated under reduced pressure. The resultant oily was purified by silica gel chromatography (hexane~hexane/toluene=10/1) to give 7.8 g of (2f) (94%).

IR ($CHCl_3$); 3022, 3018, 2969, 2939, 2886, 1588, 1573, 1485, 1468, 1443, 1422, 1389, 1290, 1264, 1255, 1227; NMR ($CDCl_3$) δ (300 $MH_z$); 2.277 (quint., J=6 Hz, 2H); 3.793 (t, J=7 Hz, 2H); 4.154 (t, J=6 Hz, 2H); 6.864 (d, J=9 Hz, 1H); 7.179 (d-d, J1=9 Hz, J2=3 Hz, 1H); 7.362 (d, J=3 Hz, 1H).

(2) Preparation of 3f; 1-[3-(2,4-Dichloro-phenoxy)-propyl]-1,2,3,6-tetrahydro-pyridine (2f) (1.7 g), 1,2,3,6-tetrahydro-pyridine (0.56 g), $K_2CO_3$ (1.85 g) and KI (0.56 g) were added to 25 ml of $CH_3CN$, and the mixture was refuxed for 13 hours. After cooling, the reaction solution was poured to water and extracted with ethyl acetate. The organic layer was washed with water and saturated saline, dried over $MgSO_4$ and the solvent was evaporated under reduced pressure. The resultant oily product was purified by silica gel chromatography (ethyl acetate/toluene=1/1~ethyl acete~ethyl acetate/methanol=10/1) to give 1.62 g of (3f) (84%). The product was recrystallized with isopropanol-diethyl ether to give the corresponding hydrochloride (3fs) as white crystals (melting point; 143.0~144.0° C.).

Elementary analysis (%): $C_{15}H_{19}C_{12}NO.HCl$; Calcd.: C=53.51, H=5.99, N=4.16, Cl=31.59, Found: C=53.47, H=5.92, N=4.25, Cl=31.40, IR (Nujol) (HCl salt); 3037, 2678, 2537, 2469, 2417, 1582, 1483, 1466, 1432, 1409, 1389, 1294, 1266, 1247, 1237; NMR ($CDCl_3$) δ (300 $MH_z$)) (Free); 2.050 (quint., J=7 Hz, 2H); 2.14~2.23 (m, 2H); 2.582 (t, J=6 Hz, 2H); 2.618 (t, J=7 Hz, 2H); 2.95~3.05 (m, 2H); 4.078 (t, J=6 Hz, 2H); 5.63~5.80 (m, 2H); 6.858 (d, J=9 Hz, 1H); 7.154 (d-d, J1=9 Hz, J2=2 Hz, 1H); 7.347 (d, J=2 Hz, 1H).

EXAMPLE 7

(1) Preparation of 2g; 1,2,3-Trichloro-4-(3-chloropropoxy)-benzene

Fifty ml of DMF solution containing of (1g) (6.8 g) and tBuOK (3.86 g) was stirred at room temperature for 1 hour. To the solution was added 1-bromo-3-chloropropane (10.83 g) and mixed at room temperature for 14 hours. The resultant reaction solution was poured to water, extracted with ethyl acetate. The organic layer was washed with water and saturated saline, dried over $MgSO_4$ and the solvent was evaporated under reduced pressure. The resultant oily product was purified by silica gel chromatography (hexane/toluene=10/1) to give 8.8g of (2 g) (93%).

IR ($CHCl_3$); 3022, 2968, 2884, 1577, 1448, 1422, 1386, 1285, 1256, 1220; NMR ($CDCl_3$) δ (300 $MH_z$); 2.290 (quint., J=6 Hz, 2H); 3.798 (t, J=6 Hz, 2H); 4.180 (t, J=6 Hz, 2H); 6.824 (d, J=9 Hz, 1H); 7.322 (d, J=9 Hz, 1H). (2) Preparation of 3g; 1-[3-(2,3,4-Trichloro-phenoxy)-propyl]-1,2,3,6-tetrahydro-pyridine (2g) (1.7 g), 1,2,3,6-tetrahydro-pyridine (0.52 g), $K_2CO_3$ (1.71 g) and KI (0.51 g) were added to 25 ml of $CH_3CN$, and the mixture was refluxed for 14 hour. After cooling, the reaction solution was poured to water and extracted with ethyl acetate. The organic layer was washed with water and saturated saline, dried over $MgSO_4$ and the solvent was evaporated under reduced pressure. The resultant oily product was purified by silica gel chromatography (ethyl acete~ethyl acetate/methanol=20/1) to give 1.90 g of (3g) (84%). The product was recrystallized with isopropanol-diethyl ether to give the corresponding hydrochloride (3gs) as white crystals (melting point; 184.0~185.0° C.).

Elementary analysis (%): $C_{14}H_{16}Cl_3NO.HCl$; Calcd.: C=47.07, H=4.80, N=3.92, Cl=39.71, Found: C=46.91, H=4.79, N=3.99, Cl=39.36, IR (Nujol) (HCl salt); 3039, 2685, 2565, 2500, 2481, 2437, 2388, 1579, 1569, 1452, 1415, 1391, 1379, 1288, 1257, NMR ($CDCl_3$) δ (300 $MH_z$) (Free); 2.060 (quint., J=7 Hz, 2H); 2.14~2.23 (m, 2H); 2.583 (t, J=6 Hz, 2H); 2.621 (t, J=7 Hz, 2H); 2.95~3.03 (m, 2H); 4.104 (t, J=6 Hz, 2H); 5.62~5.80 (m, 2H); 6.820 (d, J=9 Hz, 1H); 7.294 (d, J=9 Hz, 1H).

EXAMPLE 8

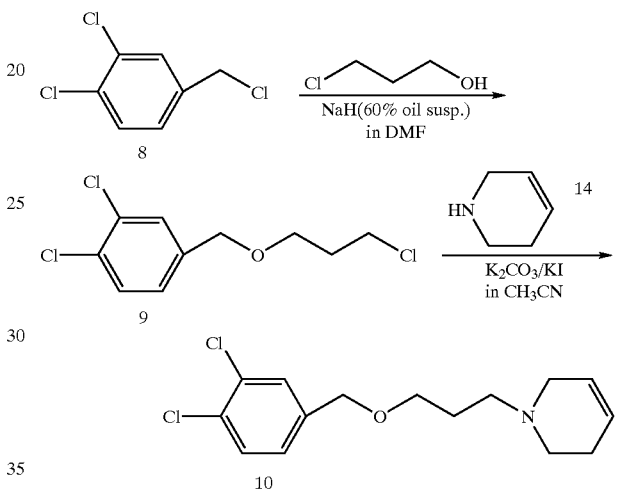

(1) Preparation of 9; 1,2-Dichloro-4-(3-chloropropoxymethyl)-benzene (8) (6 g), sodium hydride (oil, 60%) (1.47 g) and 3-chloro-1-propanol (3.78 g) were added to 35 ml of DMF under ice cooling and the mixture was stirred for 1 hour, then, reacted for 12 hours at room temperature. The reaction solution was poured to ice-water and extracted with ethyl acetate. The organic layer was washed with water and saturated saline, dried over $MgSO_4$ and the solvent was evaporated under reduced pressure. The resultant oily product was purified by silica gel chromatography (hexane/toluene=10/1~toluene) to give 3 g of (9) (39%).

IR ($CHCl_3$); 3021, 3012, 2964, 2920, 2867, 1595, 1564, 1472, 1450, 1389, 1352, 1300, 1277, 1263; NMR ($CDCl_3$) δ (300 $MH_z$); 2.064 (quint., J=6 Hz, 2H); 3.621 (t, J=6 Hz, 2H); 3.673 (t, J=6 Hz, 2H); 4.465 (s, 2H); 7.13~7.18 (m, 1H); 7.40~7.44 (m, 2H).

(2) Preparation of 10; 1-[3-(3,4-Dichloro-benzyloxy)-propyl]-1,2,3,6-tetrahydro-pyridine (9) (1.7 g), 1,2,3,6-tetrahydro-pyridine (0.56 g), $K_2CO_3$ (1.85 g) and KI (0.56 g) were added to 25 ml of $CH_3CN$ and the mixture was refluxed for 12 hours. After cooling, the reaction solution was poured to water and extracted with ethyl acetate. The organic layer was washed with water and saturated saline, dried over $MgSO_4$ and the solvent was evaporated under reduced pressure. The resultant oily product was purified by silica gel chromatography (ethyl acete~ethyl acetate/methanol=10/1) to give 1.55 g of (10) (77%). The product was recrystallized with methanol-isopropanol to give the corresponding hydrochloride (10s) as white crystals (melting point; 126.0~127.0° C.).

Elementary analysis (%): $C_{14}H_{17}Cl_2NO \cdot HCl$; Calcd.: C=52.11, H=5.62, N=4.34, Cl=32.96, Found: C=52.06, H=5.60, N=4.40, Cl=32.81, IR (Nujol) (HCl salt); 3046, 2679, 2533, 2506, 2428, 1469, 1457, 1418, 1385, 1348, 1299, 1267; NMR (CDCl$_3$) δ (300 MH$_z$) (Free); 1.857 (quint., J=7 Hz, 2H); 2.10~2.22 (m, 2H); 2.506 (t, J=8 Hz, 2H); 2.554 (t, J=6 Hz, 2H); 2.90~3.00 (m, 2H); 3.536 (t, J=6 Hz, 2H); 4.445 (s, 2H); 5.60~5.80 (m, 2H); 7.157 (d-d, J1=9 Hz, J2=2 Hz, 1H); 7.402 (d, J=9 Hz, 1H); 7.429 (d, J=2 Hz, 1H).

EXAMPLE 9

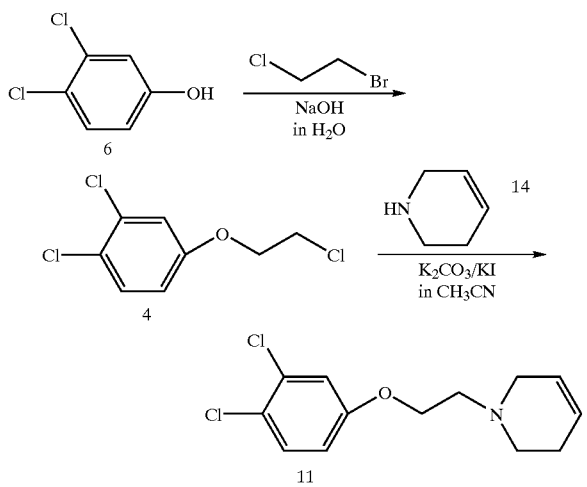

(1) Preparation of 4; 1,2-Dichloro-4-(2-chloroethoxy)-benzene

To the mixture of (1c) (10 g), 1-bromo2-chloroethane (22 g) and NaOH (4.2 g) was added 125 ml of water and the mixture was refluxed for 9 hours. After the reaction solution was cooled, the solution was extracted with diethyl ether. The organic layer was washed with water and saturated saline, dried over MgSO$_4$ and the solvent was evaporated under reduced pressure. The resultant oily product was distilled under reduced pressure to give 12 g of the compound (4) (87%), boiling point 80~83° C./1 mmHg.

IR (CHCl$_3$); 3021, 2965, 2938, 2874, 1595, 1570, 1475, 1455, 1429, 1389, 1294, 1283, 1229, 1220, 1213, NMR (CDCl$_3$) δ (200 MH$_z$); 3.804 (t, J=6 Hz, 2H); 4.202 (t, J=6 Hz, 2H); 6.785 (dd, J1=9 Hz, J2=3 Hz, 1H); 7.022 (d, J=3 Hz, 1H); 7.343 (d, J=9 Hz, 1H).

(2) Preparation of 11; 1-[2-(3,4-Dichloro-phenoxy)-ethyl]-1,2,3,6-tetrahydro-pyridine (4) (2 g), 1,2,3,6-tetrahydro-pyridine (0.81 g), K$_2$CO$_3$ (2.45 g) and KI (0.74 g) were added to 45 ml of DMF and the mixture was stirred at 95° C. for 10 hours. After cooling, the reaction solution was poured to water and extracted with ethyl acetate. The organic layer was washed with water and saturated saline, dried over MgSO$_4$ and the solvent was evaporated under reduced pressure. The resultant oily product was purified by silica gel chromatography (toluene/ethyl acetate=3/1) to give 1.0 g of (11) (41%). The product was recrystallized with methanol-isopropanol to give the corresponding hydrochloride (11s) as white crystals (melting point; 198~200° C. (decomposition)).

Elementary analysis (%): $C_{13}H_{17}Cl_2NO \cdot HCl \cdot 0.25H_2O$; Calcd.: C=49.86, H=5.31, N=4.47, Cl=33.97, Found: C=49.71, H=5.25, N=4.68, Cl=34.62, IR (Nujol) (HCl salt); 3095, 3069, 2702, 2677, 2652, 2583, 2541, 2505, 1594, 1569, 1475, 1455, 1445, 1426, 1397, 1287; NMR (CDCl$_3$) δ (200 MH$_z$) (Free); 2.16~2.25 (m, 2H); 2.684 (t, J=6 Hz, 2H); 2.864 (t, J=6 Hz, 2H); 2.05~3.16 (m, 2H); 4.099 (t, J=6 Hz, 2H); 5.60~5.82 (m, 2H); 6.767 (d-d, J1=9 Hz, J2=3 Hz, 1H); 7.009 (d, J=3 Hz, 1H); 7.311 (d, J=9 Hz, 1H).

EXAMPLE 10

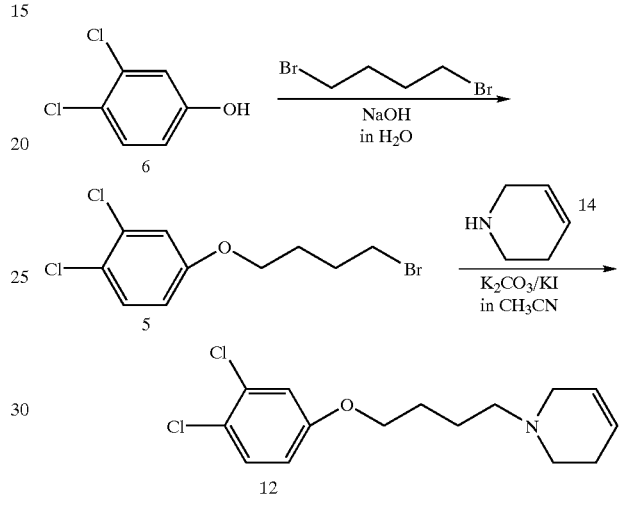

(1) Preparation of 5; 4-(4-Bromobutoxy)-1,2-dichloro-benzene

To a mixture of (1c) (10 g), 1,4-dibromobutane (19.8 g), and NaOH (2.7 g) was added 80 ml of water, then the mixture was refluxed for 7 hours. After the reaction solution was cooled, the solution was extracted with diethyl ether. The organic layer was washed with water and saturated saline, dried over MgSO$_4$ and the solvent was evaporated under reduced pressure. The resultant oily product was distilled under reduced pressure to give 13.5 g of the compound (5) (74%), boiling point 133~136° C./1 mmHg.

IR (CHCl$_3$); 3022, 2949, 2878, 1594, 1567, 1479, 1469, 1389, 1296, 1285, 1259, 1228, 1213; NMR (CDCl$_3$) δ (300 MH$_z$); 1.90~2.10 (m, 4H); 3.483 (t, J=6 Hz, 2H); 3.963 (t, J=6 Hz, 2H); 6.744 (d-d, J1=9 Hz, J2=3 Hz, 1H); 6.983 (d, J=3 Hz, 1H); 7.317 (d, J-9 Hz, 1H).

(2) Preparation of 12; 1-[4-(3,4-Dichloro-phenoxy)-butyl]-1,2,3,6-tetrahydro-pyridine (5) (1.5 g), 1,2,3,6-tetrahydro-pyridine (0.50 g), K$_2$CO$_3$ (1.39 g) and KI (0.42 g) were added to 25 ml of CH$_3$CN and the mixture was refluxed for 11 hours. After cooling, the reaction solution was poured to water and extracted with ethyl acetate. The organic layer was washed with water and saturated saline, dried over MgSO$_4$ and the solvent was evaporated under reduced pressure. The resultant oily product was purified by silica gel chromatography (ethyl acetate/toluene 1/1~ethyl acetate) to give 1.44 g of (12) (95%). The product was recrystallized with methanol-diethyl ether to give the corresponding hydrochloride (12s) as white crystals (melting point; 166.0~167.0° C.).

Elementary analysis (%): $C_{15}H_{19}Cl_2NO·HCl$; Calcd.: C=53.51, H=5.99, N=4.16, Found: C=53.44, H=6.02, N=4.24, IR (Nujol) (HCl salt); 3043, 2665, 2527, 2500, 2427, 2370, 1594, 1565, 1484, 1472, 1419, 1378, 1300, 1261, 1235; NMR (CDCl$_3$) δ (300 MH$_z$) (Free); 1.60~1.88 (m, 4H); 2.14~2.24 (m, 2H); 2.459 (t, J=7 Hz, 2H); 2.558 (t, J=6 Hz, 2H); 2.94~3.00 (m, 2H); 3.947 (t, J=6 Hz, 2H); 5.62~5.80 (m, 2H); 6.743 (d-d, J1=9 Hz, J2=3 Hz, 1H); 6.979 (d, J=3 Hz, 1H); 7.301 (d, J=9 Hz, 1H).

EXAMPLE 11

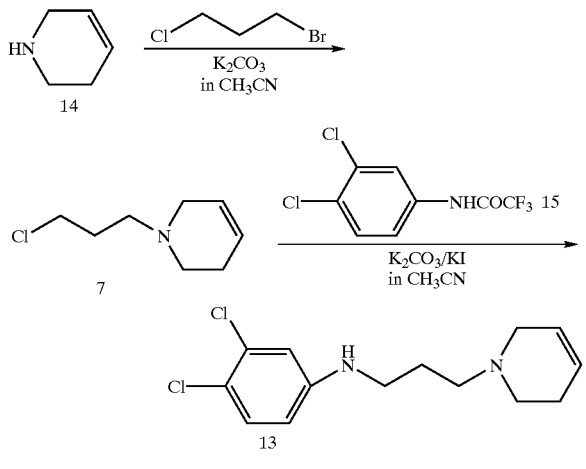

(1) Preparation of 7; 1-(3-Chloropropyl)-1,2,3,6-tetrahydro-pyridine 1,2,3,6-Tetrahydro-pyridine (14) (4.5 g), K$_2$CO$_3$ (15 g) and 1-bromo-3-chloropropane (17.05 g) were added to 150 ml of CH$_3$CN solution and the mixture was stirred at room temperature for 15 hours. The resultant reaction solution was filtrated and the solvent was evaporated under reduced pressure. The resultant oily product was purified by silica gel chromatography (ethyl acetate/toluene=1/1~ethyl acetate) to give 4.1 g of (7) (47%).

IR (CHCl$_3$); 3036, 3016, 2959, 2920, 2811, 1467, 1445, 1434, 1373, 1345, 1335, 1298, 1279, 1249, 1230, 1224, 1207; NMR (CDCl$_3$) δ (300 MH$_z$); 1.996 (quint., J=7 Hz, 2H); 2.16~2.24 (m, 2H); 2.540 (t, J=4 Hz, 2H); 2.559 (t, J=5 Hz, 2H); 2.93~3.00 (m, 2H); 3.612 (t, J=6 Hz, 2H); 5.62~5.80 (m, 2H).

(2) Preparation of 13; (3,4-Dichlorophenyl)-[3-(3,6-dihydro-2-H-pyridin-1-yl)propyl]-amine (7) (2 g), (15) (3.88 g), K$_2$CO$_3$ (3.46 g) and KI (1.04 g) were added to 25 ml of CH$_3$CN and the mixture was refluxed for 14 hours. After cooling, the reaction solution was poured to water, extracted with ethyl acetate. The organic layer was washed with water and saturated saline, dried over MgSO$_4$ and the solvent was evaporated under reduced pressure. The resultant oily product was purified by silica gel chromatography (toluene/ethyl acetate=1/1~ethyl acetate) to give 1.57 g of (13) (44%). The product was recrystallized with isopropanol-diethyl ether to give the corresponding hydrochloride (13s) as white crystals (melting point; 189.5~191.5° C.).

Elementary analysis (%): $C_{14}H_{18}Cl_2N_2·2HCl·0.75H_2O$; Calcd.: C=45.25, H=5.83, N=7.54, Found: C=45.41, H=5.81, N=7.66, IR (Nujol) (HCl salt); 3327, 3238, 2669, 2618, 2562, 2514, 2430, 1600, 1504, 1474, 1466, 1422, 1378, 1346, 1324, 1291, 1275, 1262; NMR (CDCl$_3$) δ (300 MH$_z$) (Free); 1.814 (quint., J=6 Hz, 2H); 2.14~2.26 (m, 2H); 2.550 (t, J=7 Hz, 2H); 2.574 (t, J=6 Hz, 2H); 2.94~3.00 (m, 2H); 3.154 (t, J=6 Hz, 2H); 4.90~5.25 (m, 2H); 5.62~5.82 (m, 2H); 6.382 (d-d, J1=9 Hz, J2=3 Hz, 1H); 6.613 (d, J=3 Hz, 1H); 7.144 (d, J=9 Hz, 1H).

According to the above examples, the compound and corresponding hydrochloride of Examples 12 to 51 are prepared.

(Abbreviate) Me: methyl n-Pr: n-propyl t-Bu: t-butyl

EXAMPLE 12

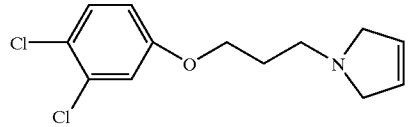

Elementary analysis (%): $C_{13}H_{15}Cl_2NO·HCl$; Calcd.: C=50.59, H=5.23, N=4.54, Cl=34.46, Found: C=50.43, H=5.12, N=4.63, Cl=34.60,

EXAMPLE 13

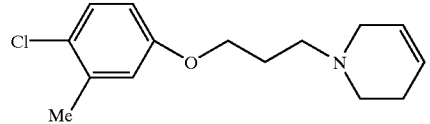

Elementary analysis (%): $C_{15}H_{20}ClNO·HCl$; Calcd.: C=59.61, H=7.00, N=4.63, Cl=23.46, Found: C=59.41, H=6.81, N=4.74, Cl=23.51, NMR (CDCl$_3$) δ ppm (300 MH$_z$) (Free); 1.997 (quint, J=7.2 Hz, 2H); 2.15~2.25 (m, 2H); 2.327 (s, 3H); 2.55~2.63 (m, 4H); 2.95~3.03 (m, 2H); 3.986 (t, J=6.3 Hz, 2H); 5.63~5.80 (m, 2H); 6.669 (dd, J1=9 Hz, J2=3 Hz, 1H); 6.774 (d, J=3 Hz, 1H); 7.198 (d, J=9 Hz, 1H).

EXAMPLE 14

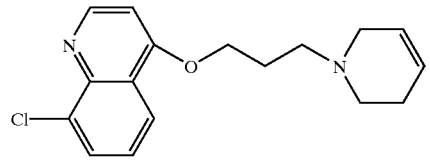

Elementary analysis (%): $C_{17}H_{19}ClN_2O·2HCl·1.20H_2O$; Calcd.: C=51.39, H=5.94, N=7.05, Cl=26.77, Found: C=51.55, H=5.88, N=7.16, Cl=27.15,

EXAMPLE 15

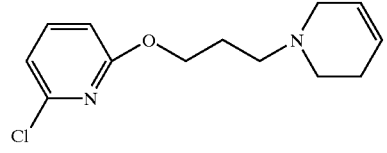

Elementary analysis (%): $C_{13}H_{17}ClN_2O·HCl$; Calcd.: C=53.99, H=6.27, N=9.69, Cl=24.52, Found: C=53.88, H=6.26, N=9.70, Cl=24.36,

EXAMPLE 16

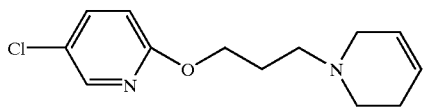

Elementary analysis (%): $C_{13}H_{17}ClN_2O \cdot 2HCl \cdot 0.2H_2O$; Calcd.: C=47.42, H=5.94, N=8.51, Cl=32.30, Found: C=47.34, H=5.82, N=8.82, Cl=31.47,

EXAMPLE 17

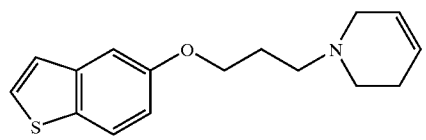

Elementary analysis (%): $C_{16}H_{19}NOS \cdot HCl \cdot 0.1H_2O$; Calcd.: C=61.66, H=6.53, N=4.49, Cl=11.38, S=10.29, Found: C=61.69, H=6.40, N=4.59, Cl=11.46, S=10.26; NMR (CDCl$_3$) δ ppm (300 MH$_z$) (Free); 2.025 (quint, J=6.3 Hz, 2H); 2.15~2.25 (m, 2H); 2.55~2.63 (m, 4H) 2.97~3.04 (m, 2H); 4.087 (t, J=6.3 Hz, 2H); 5.64~5.80 (m, 2H); 6.991 (dd, J1=8.7 Hz, J2=2.4 Hz, 1H); 7.22~7.32 (m, 2H); 7.417 (d, J=2.4 Hz, 1H); 7.714 (d, J=8.7 Hz, 1H).

EXAMPLE 18

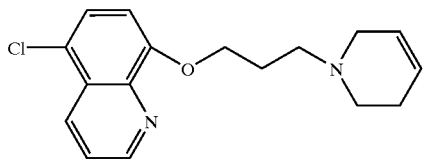

Elementary analysis (%): $C_{17}H_{19}ClN_2O \cdot 2HCl \cdot 0.8H_2O$; Calcd.: C=52.34, H=5.84, N=7.28, Found: C=52.49, H=6.38, N=6.64,

EXAMPLE 19

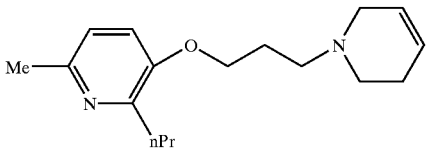

Elementary analysis (%): $C_{17}H_{26}N_2O \cdot 2HCl \cdot 0.5H_2O$; Calcd.: C=57.30, H=8.20, N=7.86, Cl=19.90, Found: C=57.16, H=8.18, N=8.07, Cl=20.37,

EXAMPLE 20

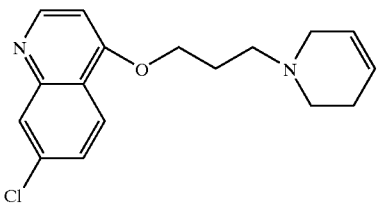

Elementary analysis (%): $C_{17}H_{19}ClN_2O \cdot 2HCl \cdot 0.5H_2O$; Calcd.: C=53.07, H=5.76, N=7.28, Cl=27.64, Found: C=53.08, H=6.07, N=7.21, Cl=27.69,

EXAMPLE 21

Elementary analysis (%): $C_{14}H_{17}Cl_2NO \cdot HCl$; Calcd.: C=52.11, H=5.62, N=4.34, Cl=32.96, Found: C=51.97, H=5.54, N=4.35, Cl=32.78, NMR (CDCl$_3$) δ ppm (300 MH$_z$); 1.999 (quint, J=7.8 Hz, 2H); 2.10~2.25 (m, 2H); 2.52~2.62 (m, 4H); 2.94~3.03 (m, 2H); 4.008 (t, J=6.3 Hz, 2H); 5.60~5.80 (m, 2H); 6.801 (d, J=1.8 Hz, 2H); 6.92~6.96 (m, 1H).

EXAMPLE 22

Elementary analysis (%): $C_{15}H_{20}ClNO \cdot HCl$; Calcd.: C=59.61, H=7.00, N=4.63, Cl=23.46, Found: C=59.57, H=6.95, N=4.70, Cl=23.30, NMR (CDCl$_3$) δ ppm (300 MH$_z$) (Free); 2.021 (quint, J=6.3 Hz, 2H); 2.10~2.24 (m, 5H); 2.54~2.65 (m, 4H); 2.95~3.03 (m, 2H); 3.994 (t, J=6 Hz, 2H); 5.60~5.80 (m, 2H); 6.721 (d, J=8.4 Hz, 1H); 7.05~7.12 (m, 2H).

EXAMPLE 23

Elementary analysis (%): $C_{15}H_{20}FNO \cdot HCl$; Calcd.: C=63.04, H=7.41, N=4.90, Cl=12.41, F=6.65; Found: C=63.00, H=7.44, N=4.94, Cl=12.33, F=6.42; NMR (CDCl$_3$) δ ppm (300 MH$_z$) (Free); 1.989 (quint, J=6.9 Hz, 2H); 2.14~2.27 (m, 5H); 2.54~2.62 (m, 4H); 2.96~3.02 (m, 2H); 3.960 (t, J=6.9 Hz, 2H); 5.62~5.80 (m, 2H); 6.61~6.74 (m, 2H); 6.885 (t, J=9 Hz, 1H).

EXAMPLE 24

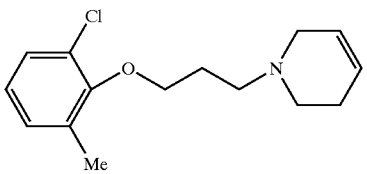

Elementary analysis (%): $C_{15}H_{20}ClNO·HCl$; Calcd.: C=59.61, H=7.00, N=4.63, Cl=23.46, Found: C=59.56, H=6.99, N=4.70, Cl=23.43,

EXAMPLE 25

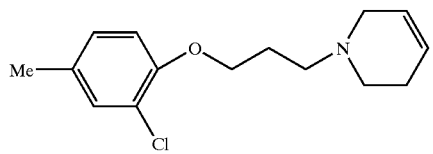

Elementary analysis (%): $C_{15}H_{20}ClNO·HCl$; Calcd.: C=59.61, H=7.00, N=4.63, Cl=23.46, Found: C=59.48, H=6.87, N=4.69, Cl=23.39, NMR (CDCl$_3$) δ ppm (300 MH$_z$) (Free); 2.041 (quint, J=6.9 Hz, 2H); 2.13~2.23 (m, 2H); 2.258 (s, 3H); 2.584 (t, J=5.7 Hz, 2H); 2.625 (t, J=6.9 Hz, 2H); 2.96~3.03 (m, 2H); 4.067 (t, J=6.3 Hz, 2H); 5.64~5.80 (m, 2H); 6.826 (d, J=8.1 Hz, 1H); 6.94~7.00 (m, 1H); 7.163 (d, J=2.1 Hz, 1H).

EXAMPLE 26

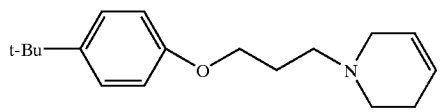

Elementary analysis (%): $C_{18}H_{27}NO·HCl·0.2H_2O$; Calcd.: C=68.97, H=9.13, N=4.47, Cl=11.31, Found: C=69.13, H=8.97, N=4.49, Cl=11.32, NMR (CDCl$_3$) δ ppm (300 MH$_z$) (Free); 1.294 (s, 9H); 2.002 (quint, J=6.3 Hz, 2H); 2.14~2.24 (m, 2H); 2.54~2.63 (m, 4H); 2.95~3.03 (m, 2H); 4.010 (t, J=6.3 Hz, 2H); 5.60~5.80 (m, 2H); 6.837 (d, J=9 Hz, 2H); 7.287 (d, J=9 Hz, 2H).

EXAMPLE 27

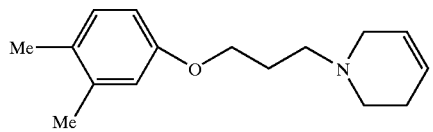

Elementary analysis (%): $C_{16}H_{23}NO·HCl$; Calcd.: C=68.19, H=8.58, N=4.97, Cl=12.58, Found: C=67.98, H=8.47, N=5.09, Cl=12.56, NMR (CDCl$_3$) δ ppm (300 MH$_z$) (Free); 1.994 (quint, J=6.6 Hz, 2H); 2.14~2.26 (m, 8H); 2.54~2.64 (m, 4H); 2.96~3.02 (m, 2H); 3.990 (t, J=6.6 Hz, 2H); 5.62~5.82 (m, 2H); 6.642 (dd, J1=8.4 Hz, J2=2.7 Hz, 1H); 6.716 (d, J=2.7 Hz, 1H); 7.011 (d, J=8.4 Hz, 1H).

EXAMPLE 28

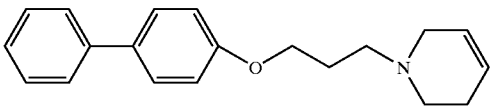

Elementary analysis (%): $C_{20}H_{23}NO·HCl·0.2H_2O$; Calcd.: C=72.04, H=7.37, N=4.20, Cl=10.63, Found: C=72.24, H=7.24, N=4.32, Cl=10.57,

EXAMPLE 29

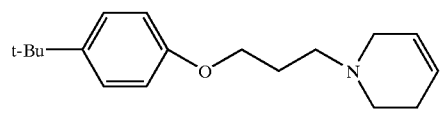

Elementary analysis (%): $C_{15}H_{20}BrNO·HCl$; Calcd.: C=51.97, H=6.11, N=4.04, Br=23.05, Cl=10.23, Found: C=51.78, H=5.89, N=4.13, Br=22.73, Cl=10.10, NMR (CDCl$_3$) δ ppm (300 MH$_z$) (Free); 1.994 (quint, J=6.0 Hz, 2H); 2.13~2.25 (m, 2H); 2.349 (s, 3H); 2.52~2.63 (m, 4H); 2.95~3.04 (m, 2H); 3.986 (t, J=6 Hz, 2H); 5.62~5.82 (m, 2H); 6.58~6.66 (m, 1H); 6.792 (d, J=3 Hz, 1H); 7.374 (d, J=9 Hz, 1H).

EXAMPLE 30

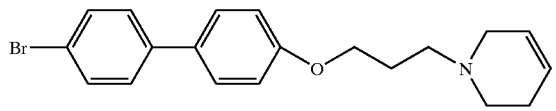

Elementary analysis (%): $C_{20}H_{22}BrNO·HCl$; Calcd.: C=58.77, H=5.67, N=3.43, Br=19.55, Cl=8.67, Found: C=58.50, H=5.52, N=3.54, Br=19.52, Cl=8.61,

EXAMPLE 31

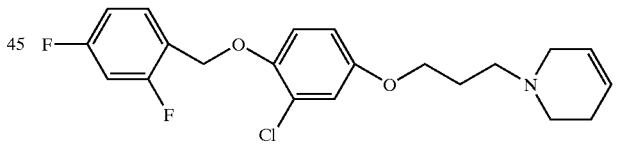

Elementary analysis (%) $C_{21}H_{22}ClF_2NO_2·HCl$; Calcd.: C=58.61, H=5.39, N=3.25, Cl=16.48, F=8.83, Found: C=58.44, H=5.32, N=3.35, Cl=16.40, F=8.64,

EXAMPLE 32

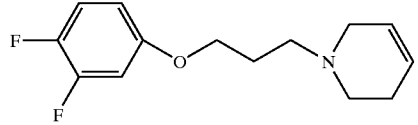

Elementary analysis (%): $C_{14}H_{17}F_2NO·HCl$; Calcd.: C=58.03, H=6.26, N=4.83, Cl=12.24, F=13.11; Found: C=57.87, H=6.32, N=4.91, Cl=12.16, F=13.03; NMR (CDCl$_3$) δ ppm (300 MH$_z$) (Free); 1.992 (quint, J=8 Hz, 2H); 2.14~2.24 (m, 2H); 2.52~2.62 (m, 4H); 2.94~3.02 (m, 2H); 3.972 (t, J=6 Hz, 2H); 5.60~5.80 (m, 2H); 6.55~6.76 (m, 2H); 6.98~7.09 (m, 1H).

EXAMPLE 33

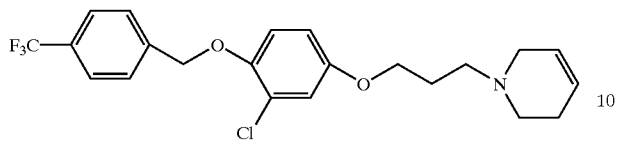

Elementary analysis (%): $C_{22}H_{23}ClF_3NO_2 \cdot HCl \cdot 0.25H_2O$; Calcd.: C=56.60, H=5.29, N=3.00, Cl=15.19, F=12.21; Found: C=56.33, H=5.22, N=3.08, Cl=15.02, F=11.97; NMR (CDCl$_3$) δ ppm (300 MH$_z$) (Free); 2.056 (quint, J=7.8 Hz, 2H); 2.15~2.24 (m, 2H); 2.55~2.68 (m, 4H); 2.96~3.03 (m, 2H); 4.072 (t, J=6.3 Hz, 2H); 5.084 (s, 2H); 5.60~5.80 (m, 2H); 6.460 (dd, J1=9 Hz, J2=2.7 Hz, 1H); 6.604 (d, J=2.7 Hz, 1H); 7.233 (d, J=9 Hz, 1H); 7.490 (d, J=8.4 Hz, 2H); 7.649 (d, J=8.4 Hz, 2H).

EXAMPLE 34

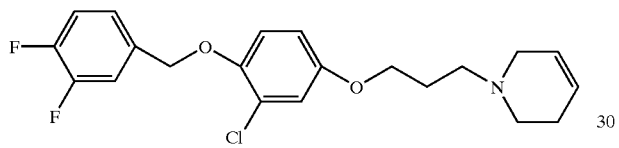

Elementary analysis (%): $C_{21}H_{22}ClF_2NO_2 \cdot HCl$; Calcd.: C=58.61, H=5.39, N=3.25, Cl=16.48, F=8.83, Found: C=58.49, H=5.45, N=3.36, Cl=16.29, F=8.54,

EXAMPLE 35

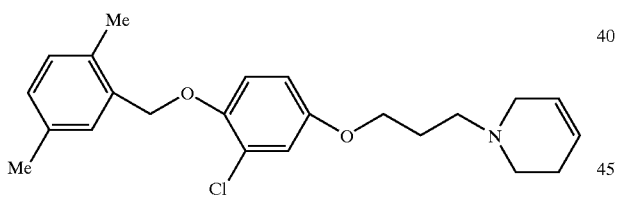

Elementary analysis (%): $C_{23}H_{28}ClNO_2 \cdot HCl$; Calcd.: C=65.40, H=6.92, N=3.32, Cl=16.79, Found: C=65.23, H=6.90, N=3.41, Cl=16.69,

EXAMPLE 36

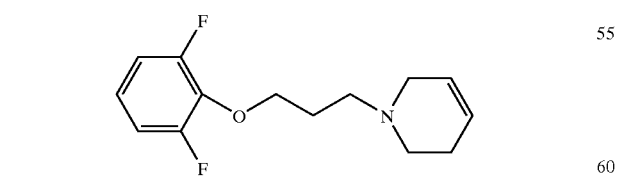

Elementary analysis (%): $C_{14}H_{17}F_2NO \cdot HCl$; Calcd.: C=58.03, H=6.26, N=4.83, Cl=12.24, F=13.11; Found: C=58.02, H=6.34, N=4.92, Cl=12.24, F=13.05; NMR (CDCl$_3$) δ ppm (300 MH$_z$) (Free); 1.988 (quint, J=6.3 Hz, 2H); 2.13~2.23 (m, 2H); 2.581 (t, J=6 Hz, 2H); 2.625 (t, J=7.2 Hz, 2H); 2.96~3.04 (m, 2H); 4.197 (t, J=6.3 Hz, 2H); 5.63~5.80 (m, 2H); 6.80~7.00 (m, 3H); 6.774 (d, J=3 Hz, 1H); 7.198 (d, J=9 Hz, 1H).

EXAMPLE 37

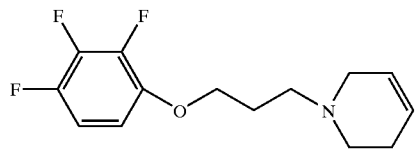

Elementary analysis (%): $C_{14}H_{16}F_3NO \cdot HCl \cdot 0.333H_2O$ Calcd.: C=53.60, H=5.68, N=4.46, Cl=11.30, F=18.17, Found: C=53.59, H=5.41, N=4.42, Cl=11.08, F=18.15, NMR (CDCl$_3$) δ ppm (300 MH$_z$) (Free); 2.030 (quint, J=6.3 Hz, 2H); 2.14~2.24 (m, 2H); 2.54~2.63 (m, 4H); 2.96~3.02 (m, 2H); 4.087 (t, J=6.3 Hz, 2H); 5.60~5.80 (m, 2H); 6.60~6.90 (m, 2H).

EXAMPLE 38

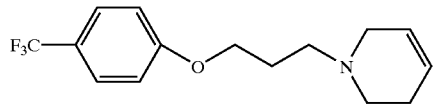

Elementary analysis (%): $C_{15}H_{18}F_3NO \cdot HCl$; Calcd.: C=55.99, H=5.95, N=4.35, Cl=11.02, F=17.71, Found: C=56.13, H=6.05, N=4.45, Cl=10.88, F=17.70,

EXAMPLE 39

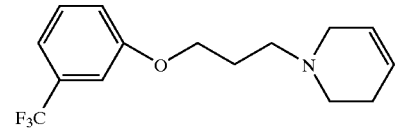

Elementary analysis (%): $C_{15}H_{18}F_3NO \cdot HCl$; Calcd.: C=55.99, H=5.95, N=4.35, Cl=11.02, F=17.71, Found: C=55.86, H=5.68, N=4.38, Cl=11.00, F=17.59, NMR (CDCl$_3$) δ ppm (300 MH$_z$) (Free); 2.032 (quint, J=6.6 Hz, 2H); 2.15~2.25 (m, 2H); 2.55~2.63 (m, 4H); 2.96~3.03 (m, 2H); 4.065 (t, J=6.6 Hz, 2H); 5.62~5.80 (m, 2H); 7.03 (m, 4H).

EXAMPLE 40

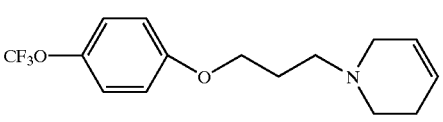

Elementary analysis (%): $C_{15}H_{18}F_3NO_2 \cdot HCl$; Calcd.: C=53.34, H=5.67, N=4.15, Cl=10.50, F=16.87, Found: C=53.41, H=5.62, N=4.15, Cl=10.39, F=16.85,

EXAMPLE 41

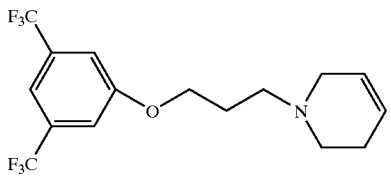

Elementary analysis (%) $C_{16}H_{17}F_6NO \cdot HCl$; Calcd.: C=49.31, H=4.65, N=3.59, Cl=9.10, F=29.25; Found: C=49.31, H=4.47, N=3.65, Cl=8.86, F=29.07; NMR (CDCl$_3$) δ ppm (300 MH$_z$) (Free); 2.056 (quint, J=6.3 Hz, 2H); 2.16~2.25 (m, 2H); 2.55~2.64 (m, 4H); 2.96~3.03 (m, 2H); 4.125 (t, J=6.6 Hz, 2H); 5.60~5.80 (m, 2 H); 7.29~7.33 (m, 2H); 7.42~7.47 (m, 1H).

EXAMPLE 42

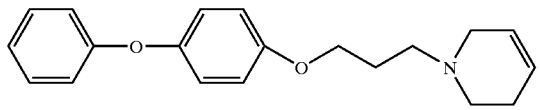

Elementary analysis (%): $C_{20}H_{23}NO_2 \cdot HCl \cdot 0.25H_2O$; Calcd.: C=68.56, H=7.05, N=4.00, Cl=10.12, Found: C=68.34, H=7.18, N=3.88, Cl=9.88,

EXAMPLE 43

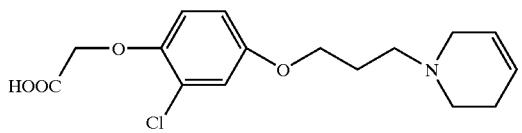

Elementary analysis (%): $C_{16}H_{20}ClNO_4 \cdot HCl$; Calcd.: C=53.05, H=5.84, N=3.87, Found: C=53.21, H=5.59, N=3.89,

EXAMPLE 44

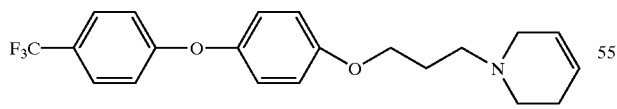

Elementary analysis (%): $C_{21}H_{22}F_3NO_2 \cdot HCl$; Calcd.: C=60.95, H=5.60, N=3.38, Cl=8.57, F=13.77, Found: C=60.86, H=5.50, N=3.45, Cl=8.55, F=13.68, NMR (CDCl$_3$) δ ppm (300 MH$_z$) (Free); 2.031 (quint, J=6.3 Hz, 2H); 2.14~2.27 (m, 2H); 2.55~2.65 (m, 4H); 2.97~3.04 (m, 2H); 4.034 (t, J=6.3 Hz, 2H); 5.65~5.83 (m, 2H); 6.90~7.04 (m, 6H); 7.534 (d, J=9 Hz, 2H).

EXAMPLE 45

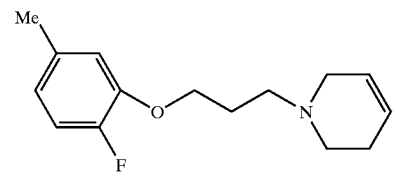

Elementary analysis (%): $C_{15}H_{20}FNO \cdot HCl$; Calcd.: C=63.04, H=7.41, N=4.90, Cl=12.41, F=6.65, Found: C=62.85, H=7.34, N=4.97, Cl=12.37, F=6.61, NMR (CDCl$_3$) δ ppm (300 MH$_z$) (Free); 2.039 (quint, J=6.3 Hz, 2H); 2.14~2.23 (m, 2H); 2.290 (s, 3H); 2.581 (t, J=5.7 Hz, 2H); 2.601 (t, J=7.5 Hz, 2H); 2.96~3.02 (m, 2H); 4.087 (t, J=6.3 Hz, 2H); 5.60~5.80 (m, 2H); 6.60~6.98 (m, 3H).

EXAMPLE 46

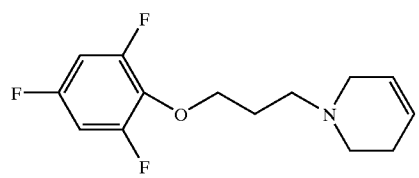

Elementary analysis (%): $C_{14}H_{16}F_3NO \cdot HCl \cdot 0.1H_2O$; Calcd.: C=54.32, H=5.60, N=4.52, Cl=11.45, F=18.41, Found: C=54.23, H=5.48, N=4.57, Cl=11.49, F=18.44, NMR (CDCl$_3$) δ ppm (300 MH$_z$) (Free); 1.976 (quint, J=6.3 Hz, 2H); 2.13~2.23 (m, 2H); 2.54~2.65 (m, 4H); 2.95~3.03 (m, 2H); 4.135 (t, J=6.3 Hz, 2H); 5.60~5.80 (m, 2H); 6.60~6.72 (m, 2H).

EXAMPLE 47

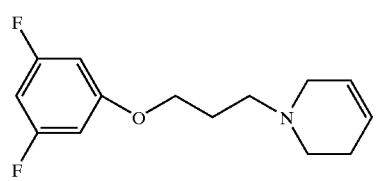

Elementary analysis (%): $C_{14}H_{17}F_2NO \cdot HCl$; Calcd.: C=58.03, H=6.26, N=4.83, Cl=12.24, F=13.11, Found: C=57.83, H=6.13, N=4.86, Cl=12.27, F=12.89, NMR (CDCl$_3$) δ ppm (300 MH$_z$) (Free); 2.005 (quint, J=7.2 Hz, 2H); 2.10~2.20 (m, 2H); 2.52~2.60 (m, 4H); 2.95~3.02 (m, 2H); 3.997 (t, J=6.3 Hz, 2H); 5.63~5.80 (m, 2H); 6.34~6.47 (m, 2H).

EXAMPLE 48

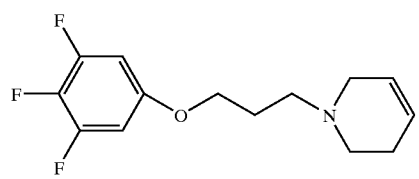

Elementary analysis (%): $C_{14}H_{16}F_3NO \cdot HCl$; Calcd.: C=54.64, H=5.57, N=4.55, Cl=11.52, F=18.52, Found: C=54.45, H=5.47, N=4.65, Cl=11.41, F=18.33,

EXAMPLE 49

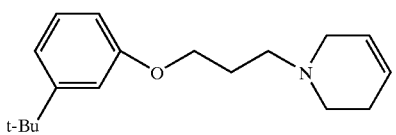

Elementary analysis (%): $C_{18}H_{27}NO \cdot HCl$; Calcd.: C=68.97, H=9.13, N=4.47, Cl=11.31, Found: C=69.70, H=9.13, N=4.62, Cl=11.42, NMR (CDCl$_3$) δ ppm (300 MH$_z$) (Free); 1.306 (s, 9H); 2.022 (quint, J=7.2 Hz, 2H); 2.14~2.24 (m, 2H); 2.55~2.64 (m, 4H); 2.90~3.03 (m, 2H); 4.028 (t, J=6.3 Hz, 2H); 5.60~5.80 (m, 2H); 6.70~7.25 (m, 2H).

EXAMPLE 50

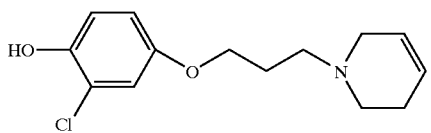

Elementary analysis (%): $C_{14}H_{18}ClNO_2 \cdot HCl$; Calcd.: C=55.27, H=6.30, N=4.60, Found: C=55.20, H=6.43, N=4.63,

EXAMPLE 51

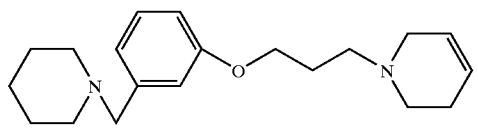

Elementary analysis (%): $C_{20}H_{30}N_2O \cdot 2HCl \cdot 0.25H_2O$; Calcd.: C=61.30, H=8.36, N=7.15, Cl=18.09, Found: C=61.62, H=8.45, N=7.23, Cl=18.12,

EXAMPLE 52

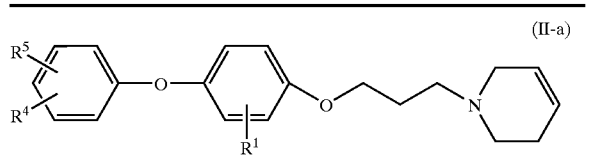

(II-a)

| No | R$^1$ | R$^4$ | R$^5$ |
|---|---|---|---|
| 1 | H | H | 4-F |
| 2 | H | H | 3-Cl |
| 3 | H | H | 2-Br |
| 4 | H | H | 4-t-Bu |
| 5 | H | H | 3-Me |
| 6 | H | 2-F | 4-F |
| 7 | H | 3-Cl | 4-Cl |
| 8 | H | 4-F | 3-Me |
| 9 | H | 3-Cl | 5-Cl |
| 10 | H | 4-Cl | 2-Me |
| 11 | H | 4-F | 3-Me |
| 12 | H | 2-Cl | 6-Me |
| 13 | H | 3-Me | 4-Me |
| 14 | H | 3-Me | 4-Br |
| 15 | H | 2-F | 6-F |

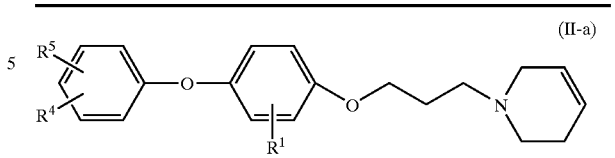

(II-a)

| No | R$^1$ | R$^4$ | R$^5$ |
|---|---|---|---|
| 16 | H | 3-CF$_3$ | 5-CF$_3$ |
| 17 | H | 2-F | 5-Me |
| 18 | 2-F | H | 4-F |
| 19 | 2-F | H | 3-Cl |
| 20 | 3-Cl | H | 2-Br |
| 21 | 3-Cl | H | 4-t-Bu |
| 22 | 2-Br | H | 3-Me |
| 23 | 3-Br | H | 4-CF$_3$ |
| 24 | 2-t-Bu | H | 3-F |
| 25 | 3-CF$_3$ | H | 3-Cl |
| 26 | 2-F | 2-F | 4-F |
| 27 | 2-F | 3-Cl | 4-Cl |
| 28 | 3-Cl | 4-F | 3-Me |
| 29 | 3-Cl | 3-Cl | 5-Cl |
| 30 | 2-OMe | 4-Cl | 2-Me |
| 31 | 3-OMe | 4-F | 3-Me |
| 32 | 2-t-Bu | 2-Cl | 6-Me |
| 33 | 3-CF$_3$ | 3-Me | 4-Me |
| 34 | 2-F | 3-Me | 4-Br |
| 35 | 2-F | 2-F | 6-F |
| 36 | 3-Cl | 3-CF$_3$ | 5-CF$_3$ |
| 37 | 3-Cl | 2-F | 5-Me |
| 38 | 2-Br | 2-F | 4-F |

Experimental Example 1

After 80 mg/kg of the present compound was administered subcutaneously for 7 days to 7–8 week aged male KK-Ay mouse (n=5~7, CLEA JAPAN, INC), the amount of food intake from seventh day to eighth day, and body weight of eighth day were measured. For a control group, physiological saline was used. After the body weight was measured, the blood was collected from abdominal aorta by a syringe containing 50 U heparin and centrifuged 12,000×g for five min. Glucose in blood was measured by New Blood.Sugar.Test (Boehringer Ingelheim) and insulin was measured by Insulin-EIA Test (GLAOZYME). The result is shown below. Each value is an average value and represented by percent to each value of eighth days in the control group. As to the compounds of and after Example 13, each corresponding hydrochloride was used.

TABLE 1

| Example (compound No.) | Dose (80 mg/kg)(S.C) | | | |
|---|---|---|---|---|
| | Body weight | Food intake | Glucose | Insulin |
| 1 (3as) | **85 | **76 | **56 | **12 |
| 2 (3bs) | *93 | 100.0 | *79 | *41 |
| 3 (3cs) | **84 | 82 | **73 | *49 |
| 4 (3ds) | **87 | **79 | 84.0 | 47.0 |
| 5 (3es) | *94 | 88.0 | *62 | *38 |
| 6 (3fs) | **85 | 84.0 | **76 | **32 |
| 7 (3gs) | **83 | **78 | **72 | 51.0 |
| 8 (10s) | 94.0 | 96.0 | *78 | *31 |
| 9 (11s) | **87 | **83 | *71 | 53 |
| 10 (12s) | *94 | *82 | 87.0 | *31 |
| 11 (13s) | *94 | 92.0 | 93.0 | 74.0 |
| 17 | *94 | **84 | 99 | 84 |
| 21 | **89 | **74 | *80 | *53 |
| 23 | **89 | **76 | 67.0 | 91 |

TABLE 1-continued

| Example (compound No.) | Dose (80 mg/kg)(S.C) | | | |
|---|---|---|---|---|
| | Body weight | Food intake | Glucose | Insulin |
| 25 | **90 | **73 | **58 | 63 |
| 27 | **93 | **77 | 87.0 | **42 |
| 29 | **90 | **78 | 87 | 66 |
| 30 | 95 | **73 | **62 | *50 |
| 32 | *92 | *85 | *73 | 69 |
| 33 | **93 | **72 | **54 | **44 |
| 36 | **86 | **75 | **61 | *54 |
| 39 | *95 | **78 | **70 | *52 |
| 41 | **88 | **77 | **56 | **48 |
| 44 | **82 | **59 | **54 | **21 |
| 45 | **94 | *82 | 79 | 70 |
| 46 | **90 | 91 | **58 | *53 |
| 49 | **91 | **80 | **56 | 73 |

In above table, * shows that the reliability of significant difference is 95% or more, ** shows that the reliability of significant difference is 99% or more. The present compound has the decrease effect of body weight, thus being for use as an antiobestic agent. In case of more preferable compounds (3bs, 3cs, 3fs and the like), food intake (Food intake) was little repressed.

Moreover, the present compound decreased remarkably Insulin and Glucose concentration in blood. Since the compound can improve insulin resistance, it is for use for the prevention and treatment of diabetes mellitus, especially, type II diabetes mellitus.

Experimental Example 2

The compound 3cs of Example 3 (40 mg/kg ) was administered subcutaneously to KK-Ay mouse. After 24 hours, the concentration of leptin in plasma was measured by using mouse leptin RIA measuring kit (Linco). The blood was collected from abdominal aorta by a syringe containing 50 U heparin and centrifuged 12,000×g for 5 min to give plasma. Result: While the plasma leptin concentration of a group being administrated physiological saline was 26.7±1.9 ng/ml, the concentration of a group with the present compound was 44.8±5.2 ng/ml, which showed a significant increase. The present compound increased the concentration of leptin in blood.

Formulation Example 1

The compound 3c of Example 3, crystalline cellulose, magnesium stearate and the like, each proper amount was mixed and the mixture was tabletted to give tablets.

Formulation Example 2

After the compound 3c of Example 3, lactose, magnesium stearate and the like, each proper amount was mixed and the mixture was extruded to give granules.

Formulation Example 3

The granule of Formulation Example 2 was capsulated to give capsules.

Industrial Applicability

The present compound is for use as an anti obestic agent, the preventive and therapeutic agent for diabetes and the like.

What is claimed is:

1. A method for treating obesity which comprises administering a compound of the formula (II):

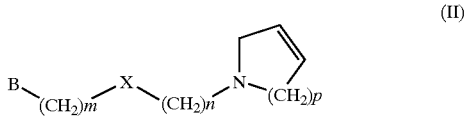

(II)

wherein B is

(a)

wherein $R^1$, $R^2$ and $R^3$ are each independently hydrogen, halogen, hydroxy, lower alkyl, halogenated lower alkyl, lower alkoxy, halogenated lower alkoxy, carboxy lower alkoxy, optionally substituted phenyl, optionally substituted phenoxy, or optionally substituted phenyl (lower) alkoxy, wherein said optional substitution is one to three members selected from the group consisting of halogen, lower alkyl, lower alkoxy, lower alkylthio, hydroxy, amino, carboxy, cyano, nitro, lower alkylcarbonyl, lower alkoxycarbonyl, halogenated lower alkyl, halogenated lower alkoxy, carboxy (lower) alkoxy, optionally substituted phenyl, optionally substituted phenoxy, and optionally substituted phenyl (lower) alkoxy, wherein the latter optional substitution is lower alkyl, halogen, halogenated lower alkyl and halogenated lower alkoxy;

$Z^1$ is CH;

X is O;

m is 0;

n is an integer of 1 to 5;

p is 2, provided that the following (1) and (2) are excluded: (1) n is 2 and B is 3,4-dimethylphenyl, 4-t-butylphenyl, 4-(t-butyl-$CH_2C(CH_3)_2$)-phenyl, 4-isopentylphenyl, 2-isopropyl-5-methylphenyl, 3-methoxyphenyl or 2-Cl, 4-Br-phenyl, (2) n is 3 and B is 2,6-dimethylphenyl, and pharmaceutically acceptable salt, or hydrate thereof, to an obese patient.

2. The method described in claim 1 excluding the compound wherein n is 2 or 3; and one or two of $R^1$, $R^2$ and $R^3$ is lower alkyl and the other is hydrogen.

3. The method described in claim 1 excluding the compound wherein n is 2; $R^1$ is lower alkoxy and $R^2$ and $R^3$ are hydrogens.

4. The method described in claim 1 wherein $R^1$ is halogen; $R^2$ and $R^3$ are each independently hydrogen, halogen or lower alkyl.

5. The method described in claim 4 wherein $R^1$ is halogen; $R^2$ and $R^3$ are each independently hydrogen or halogen.

6. The method described in claim 1 wherein $R^1$ is halogenated lower alkyl, $R^2$ is hydrogen or halogenated lower alkyl, $R^3$ is hydrogen.

7. The method described in claim 1 wherein n is 2 or 3.

8. The method described in claim 1 wherein $R^1$ is halogen, $R^2$ and $R^3$ are each independently hydrogen, halogen or alkyl and n is 3.

9. The method described in claim 8 wherein $R^1$ is halogen; $R^2$ and $R^3$ are each independently hydrogen or halogen; n is 3.

10. The method described in claim 1 wherein $R^1$ is halogenated lower alkyl, $R^2$ is hydrogen or halogenated lower alkyl, $R^3$ is hydrogen, and n is 3.

11. The method described in claim 1 wherein $R^1$ is optionally substituted phenoxy; $R^2$ and $R^3$ are hydrogens; and n is 2 to 4.

12. The method described in claim 1 wherein $R^1$ is phenoxy substituted with halogenated lower alkyl; $R^2$ and $R^3$ are hydrogens; and n is 2 to 4.

13. A composition for use as an antiobestic agent containing a compound of the formula (II):

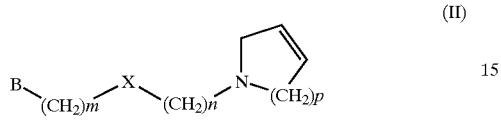

(II)

wherein B is

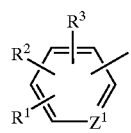

(a)

wherein $R^1$, $R^2$ and $R^3$ are each independently hydrogen, halogen, hydroxy, lower alkyl, halogenated lower alkyl, lower alkoxy, halogenated lower alkoxy, carboxy lower alkoxy, optionally substituted phenyl, optionally substituted phenoxy, or optionally substituted phenyl (lower) alkoxy, wherein said optional substitution is with one to three members selected from the group consisting of halogen, lower alkyl, lower alkoxy, lower alkylthio, hydroxy, amino, carboxy, cyano, nitro, lower alkylcarbonyl, lower alkoxycarbonyl, halogenated lower alkyl, halogenated lower alkoxy, carboxy (lower) alkoxy, optionally substituted phenyl, optionally substituted phenloxy, and optionally substituted phenyl (lower) alkoxy, wherein the latter optional substitution is lower alkyl, halogen, halogenated lower alkyl and halogenated lower alkoxy;

$Z^1$ is CH;

X is O;

m is 0;

n is an integer of 1 to 5;

p is 2, provided that the following (1) and (2) are excluded: (1) n is 2 and B is 3,4-dimethylphenyl, 4-t-butylphenyl, 4-(t-butyl-$CH_2C(CH_3)_2$)-phenyl, 4-isopentylphenyl, 2-isopropyl-5-methylphenyl, 3-methoxyphenyl or 2-Cl, 4-Br-phenyl, (2) n is 3 and B is 2,6-dimethylphenyl, and pharmaceutically acceptable salt, or hydrate thereof and a pharmaceutically acceptable carrier.

* * * * *